(12) United States Patent
Smith et al.

(10) Patent No.: US 12,208,269 B2
(45) Date of Patent: Jan. 28, 2025

(54) CALIBRATION FOR ECAP SENSING

(71) Applicant: Medtronic, Inc., Minneapolis, MN (US)

(72) Inventors: Todd V. Smith, Shoreview, MN (US); Robert A. Corey, Arden Hills, MN (US); Heba Tareq Omar, Blaine, MN (US); Kristin N. Hageman, Dayton, MN (US)

(73) Assignee: Medtronic, Inc., Minneapolis, MN (US)

( * ) Notice: Subject to any disclaimer, the term of this patent is extended or adjusted under 35 U.S.C. 154(b) by 380 days.

(21) Appl. No.: 17/654,695

(22) Filed: Mar. 14, 2022

(65) Prior Publication Data

US 2023/0285754 A1   Sep. 14, 2023

(51) Int. Cl.
*A61N 1/36*   (2006.01)
*A61N 1/05*   (2006.01)

(52) U.S. Cl.
CPC ....... *A61N 1/36139* (2013.01); *A61N 1/0551* (2013.01); *A61N 1/36153* (2013.01); *A61N 1/36062* (2017.08)

(58) Field of Classification Search
None
See application file for complete search history.

(56) References Cited

U.S. PATENT DOCUMENTS

| 4,203,670 A | 5/1980 | Bromberg | |
| 4,903,700 A * | 2/1990 | Whigham | A61N 1/365 607/13 |
| 4,991,583 A * | 2/1991 | Silvian | A61N 1/36185 607/13 |
| 5,330,512 A * | 7/1994 | Hauck | A61N 1/3706 607/28 |
| 9,386,934 B2 | 7/2016 | Parker et al. | |
| 9,950,171 B2 | 4/2018 | Johanek et al. | |

(Continued)

FOREIGN PATENT DOCUMENTS

WO   2021026151 A1   2/2021

OTHER PUBLICATIONS

International Search Report and Written Opinion of International Application No. PCT/IB2023/052200 dated Jun. 5, 2023, 12 pp.

(Continued)

*Primary Examiner* — Carl H Layno
*Assistant Examiner* — Manolis Pahakis
(74) *Attorney, Agent, or Firm* — Shumaker & Sieffert, P.A.

(57) ABSTRACT

Systems, devices, and techniques are described for calibrating a medical device that senses ECAP signals from a patient's nerve tissue. For example a method includes instructing, with processing circuitry, stimulation circuitry of a medical device to deliver, on stimulation electrodes of the medical device, an electrical stimulation signal having an amplitude substantially equal to zero to a patient, entering, with the processing circuitry subsequent to instructing the stimulation circuitry to deliver the electrical stimulation signal, a passive recharge state on stimulation electrode circuitry, and auto-zeroing, with the processing circuitry, inputs to an operational amplifier of sensing circuitry electrically coupled to sensing electrodes of the medical device while the stimulation electrode circuitry is in the passive recharge state.

20 Claims, 8 Drawing Sheets

(56) References Cited

U.S. PATENT DOCUMENTS

| | | | |
|---|---|---|---|
| 10,183,168 B2 | 1/2019 | Baru et al. | |
| 10,278,600 B2 | 5/2019 | Parker et al. | |
| 10,926,092 B2 | 2/2021 | Esteller et al. | |
| 11,129,991 B2* | 9/2021 | Dinsmoor | A61N 1/36175 |
| 2008/0284507 A1 | 11/2008 | Pertijs et al. | |
| 2009/0082691 A1 | 3/2009 | Denison et al. | |
| 2015/0119751 A1* | 4/2015 | Stanslaski | A61N 1/3605 |
| | | | 600/554 |
| 2015/0223710 A1* | 8/2015 | Cong | A61B 5/24 |
| | | | 600/554 |
| 2018/0132747 A1 | 5/2018 | Parker et al. | |
| 2018/0243564 A1* | 8/2018 | Stanslaski | A61N 1/3615 |
| 2018/0353760 A1 | 12/2018 | Bonnet et al. | |
| 2019/0190296 A1* | 6/2019 | Paralikar | A61N 1/3787 |
| 2019/0388692 A1 | 12/2019 | Dinsmoor et al. | |
| 2019/0388695 A1* | 12/2019 | Dinsmoor | A61B 5/4836 |
| 2020/0029914 A1 | 1/2020 | Single | |
| 2020/0266824 A1 | 8/2020 | Smith et al. | |
| 2020/0316382 A1 | 10/2020 | Esteller | |
| 2021/0008365 A1 | 1/2021 | Feldman et al. | |
| 2021/0187298 A1 | 6/2021 | Dinsmoor et al. | |
| 2022/0008731 A1* | 1/2022 | Dinsmoor | A61B 5/4836 |
| 2023/0264014 A1* | 8/2023 | Corey | A61N 1/36139 |
| | | | 607/2 |
| 2024/0009463 A1* | 1/2024 | Dinsmoor | A61B 5/686 |

OTHER PUBLICATIONS

Zhuangguang et al., "A charge balancing technique for neurostimulators", Analog Integrated Circuits and Signal Processing, vol. 105, No. 3, Springer New York LLC, US, Oct. 9, 2020, pp. 483-496.

U.S. Appl. No. 18/161,499, filed Jan. 30, 2023, naming inventors Corey et al.

* cited by examiner

CALIBRATION FOR ECAP SENSING

TECHNICAL FIELD

This disclosure generally relates to electrical stimulation, and more specifically, control of electrical stimulation.

BACKGROUND

Medical devices may be external or implanted and may be used to deliver electrical stimulation to patients via various tissue sites to treat a variety of symptoms or conditions such as chronic pain, tremor, Parkinson's disease, epilepsy, urinary or fecal incontinence, sexual dysfunction, obesity, or gastroparesis. A medical device may deliver electrical stimulation therapy via one or more leads that include electrodes located proximate to target locations associated with the brain, the spinal cord, pelvic nerves, peripheral nerves, or the gastrointestinal tract of a patient. Stimulation proximate the spinal cord, proximate the sacral nerve, within the brain, and proximate peripheral nerves are often referred to as spinal cord stimulation (SCS), sacral neuromodulation (SNM), deep brain stimulation (DBS), and peripheral nerve stimulation (PNS), respectively. Electrical stimulation often results in evoked compound action potentials (ECAPs) from nerves within the patient.

SUMMARY

In general, systems, devices, and techniques are described for calibrating the sensing circuitry of a medical device that delivers electrical stimulation therapy to a patient and senses evoked action potential (ECAP) signals from the patient's nerve tissue. ECAP signals are a measure of the nerve tissue's response to stimulation. For instance, in response to a stimulation, a nerve generates an ECAP signal, and the parameters of the ECAP signal, such as amplitude, may be a function of how much the nerve responded to the stimulation. Medical devices can provide more effective therapy by adjusting an amount of stimulation based on sensed ECAP signals. ECAP signals are relatively small and variable, and the medical device that delivers electrical stimulation therapy may contain residual charge from each stimulation. Accordingly, there may be technical problems for sensing circuitry to properly resolve ECAP signals (e.g., difficult to distinguish ECAP signals from noise). Thus, sensing circuitry of the medical device may be calibrated regularly to accurately measure the amplitude of an ECAP signal.

Sensing circuitry may be effectively calibrated when facing the same internal conditions as the sensing circuitry faces during sensing. The internal conditions faced by the sensing circuitry may vary with the state of the stimulation circuitry of the medical device. In one or more examples described in this disclosure, calibrating the sensing circuitry may be considered as auto-zeroing the sensing circuitry. However, to effectively perform auto-zeroing, the medical device may configure the sensing circuitry and the stimulation circuitry into particular states, such as the state of the sensing circuitry and stimulation circuitry when the sensing circuitry is to be used to sense signals. In this way, the example techniques describe ways in which to improve the operation of the medical device circuitry to more accurately sense signals, such as relatively small signals like ECAP signals.

For example, a method may include: instructing, with processing circuitry, stimulation circuitry of a medical device to deliver, on stimulation electrodes of the medical device, an electrical stimulation signal having an amplitude substantially equal to zero to a patient; entering, with the processing circuitry subsequent to instructing the stimulation circuitry to deliver the electrical stimulation signal, a passive recharge state on stimulation electrode circuitry; and auto-zeroing, with the processing circuitry, inputs to an operational amplifier of sensing circuitry electrically coupled to sensing electrodes of the medical device while the stimulation electrode circuitry is in the passive recharge state.

In some examples, a system may include a medical device, wherein the medical device includes: sensing circuitry comprising an operational amplifier and electrically couplable to sensing electrodes; stimulation circuitry electrically couplable to stimulation electrodes; and processing circuitry configured to: instruct the stimulation circuitry to deliver, on the stimulation electrodes, an electrical stimulation signal having an amplitude substantially equal to zero to a patient; enter, subsequent to instructing the stimulation circuitry to deliver the electrical stimulation signal, a passive recharge state on stimulation electrode circuitry; and auto-zero inputs to the operational amplifier of the sensing circuitry while the stimulation electrode circuitry is in the passive recharge state.

In some examples, a computer-readable storage medium comprising instructions that, when executed by processing circuitry of a medical device, cause the processing circuitry to: instruct stimulation circuitry to deliver, on stimulation electrodes, an electrical stimulation signal having an amplitude substantially equal to zero to a patient; enter, subsequent to instructing the stimulation circuitry to deliver the electrical stimulation signal, a passive recharge state on stimulation electrode circuitry; and auto-zero inputs to an operational amplifier of sensing circuitry of the medical device while the stimulation electrode is in the passive recharge state.

The summary is intended to provide an overview of the subject matter described in this disclosure. It is not intended to provide an exclusive or exhaustive explanation of the systems, device, and methods described in detail within the accompanying drawings and description below. Further details of one or more examples of this disclosure are set forth in the accompanying drawings and in the description below. Other features, objects, and advantages of the techniques will be apparent from the description and drawings, and from the claims.

DETAILED DESCRIPTION

Figure 1:
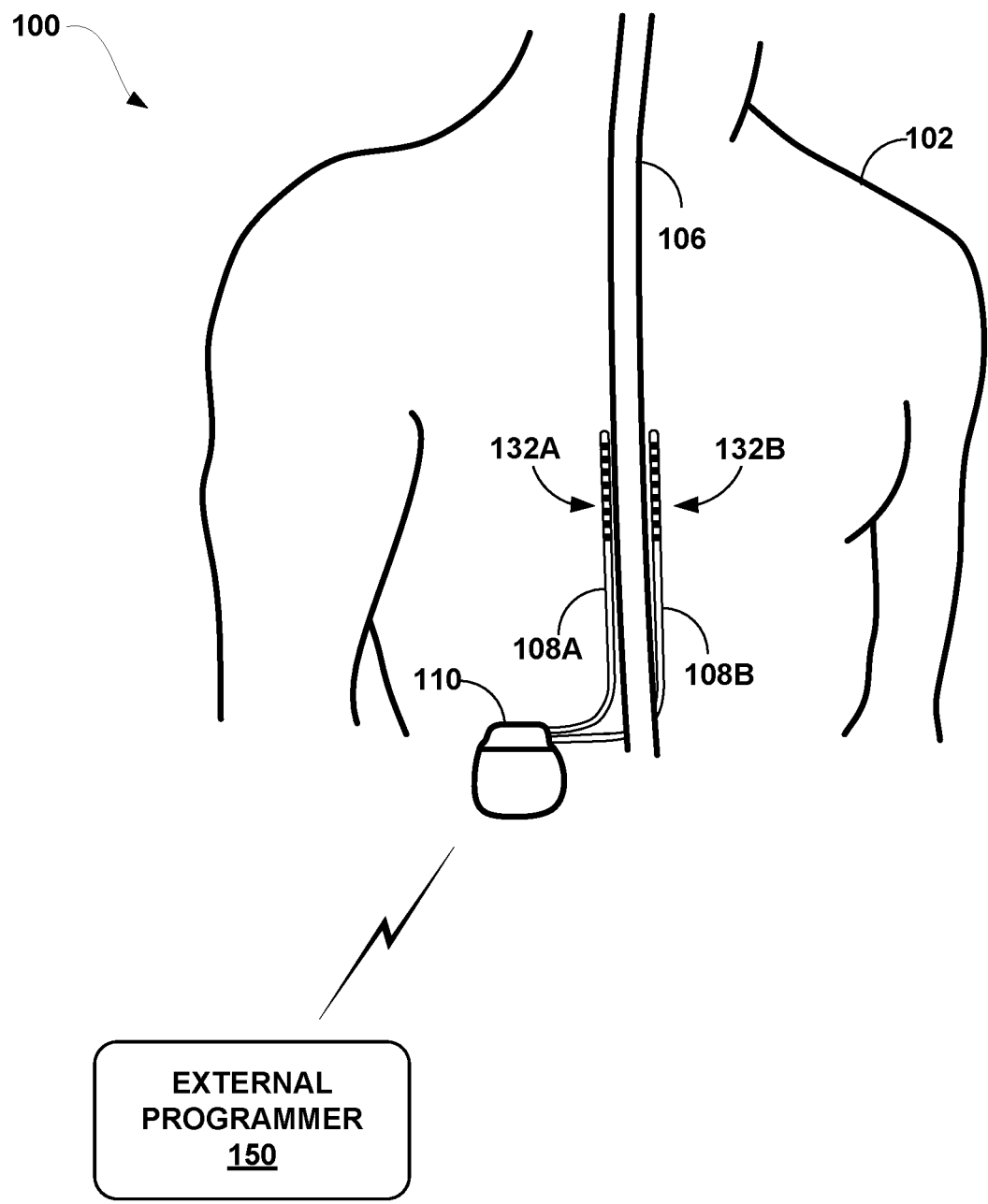
FIG. 1 is a conceptual diagram illustrating an example system that includes an implantable medical device (IMD) according to the techniques of the disclosure.

The disclosure describes examples of medical devices, systems, and techniques for calibrating medical devices (e.g., sensing circuitry of medical devices) configured to provide electrical stimulation therapy. Electrical stimulation therapy is typically delivered to a target tissue (e.g., nerves of the spinal cord or muscle) of a patient via two or more electrodes. The two or more electrodes may deliver control pulses configured to elicit an evoked compound action potential (ECAP) signal from nerve tissue of a patient, or deliver informed pulses configured to deliver therapy to the patient. In this disclosure, "control pulses" may be stimulation pulses that are used to elicit the ECAP signal. The control pulses may provide therapeutic effect, but need not necessarily provide therapeutic effect. "Informed pulses" may be stimulation pulses that provide therapeutic effect. Informed pulses may be "informed" in the sense that the parameters of the informed pulses (e.g., amplitude, pulse width, frequency, etc.) may be based on the sensing of the ECAP signal that was generated due to the control pulses. The informed pulses may be considered as providing governing therapy or governed therapy. Governing therapy or governed therapy may indicate that the stimulation pulses are for effective therapy.

Parameters of the electrical stimulation therapy (e.g., electrode combination, voltage or current amplitude, pulse width, pulse frequency, etc.) may be selected by a clinician and/or the patient to provide relief from various symptoms, such as pain, nervous system disorders, muscle disorders, etc. In addition, electrical stimulation therapy may be informed by the measured ECAPs, that is, parameters of the electrical stimulation therapy (e.g., informed pulses) may be adjusted in response to measured ECAPs. In order to accurately measure ECAPs and provide more effective therapy, sensing circuitry configured to sense ECAPs may be effectively calibrated.

To be effectively calibrated, sensing circuitry of an IMD should be calibrated when the IMD circuitry is in the same state as when the sensing circuitry would be sensing an ECAP signal. The IMD circuitry may include the sensing circuitry, control electrode circuitry, stimulation circuitry, and other circuitry necessary to perform the operations of the IMD. Generally, an IMD may sense for ECAP signals when control electrode circuitry of the IMD is in a state of passive recharge, i.e., after control electrodes of the IMD deliver a control pulse configured to elicit the ECAP signal. When the control electrode circuitry is in a passive recharge state, coupling capacitors of the control electrode circuitry may be connected to one another in a circuit loop to discharge any residual charge that may have built up on the electrodes and surrounding tissue. For example, the coupling capacitors may both be coupled to ground within the IMD circuitry ("IMD ground"), forming a loop between the coupling capacitors that may drain residual charge across the coupling capacitors.

In some examples, after the control electrodes deliver the control pulse, the control electrode circuitry (including the control electrodes) may enter an active recharge state to quickly drain developed charge within the control electrode circuitry, followed by a passive recharge state to continue reducing developed charge. In an active recharge state, the control electrodes may deliver an electrical stimulation signal having the opposite polarity as the electrical stimulation signal delivered for therapy so that there is not a buildup of charge in the tissue. Because sensing circuitry of the IMD senses for ECAP signals during this passive recharge state on the control electrodes, sensing circuitry should be calibrated when the control electrode circuitry is in the passive recharge state in order to get the most accurate calibration of the ECAP sensors.

To elicit a passive recharge state in the control electrode circuitry, the IMD may be programmed to deliver an electrical stimulation signal having an amplitude substantially equal to zero on the control electrodes. For example, processing circuitry of the IMD may instruct the control electrode circuitry to deliver an electrical stimulation signal having an amplitude substantially equal to zero (also called a "ghost pulse"). Delivering a ghost pulse on the control electrodes may initiate an active recharge and passive recharge cycle on the control electrode circuitry without adding any unnecessary charge to patient tissue or the circuitry of the IMD. Once the control electrode circuitry enters the passive recharge state following the ghost pulse, processing circuitry may calibrate the sensing circuitry. That is, an internal state machine of the IMD circuitry may be configured to enter the control electrode circuitry into a passive recharge state after stimulation is delivered. However, for purposes of calibration, no stimulation signal is needed, but the state machine may need to first have a stimulation pulse that is delivered before the state machine can transition the stimulation electrode circuitry to the passive recharge state. Accordingly, by instructing the stimulation circuitry to deliver an electrical stimulation signal having an amplitude substantially equal to zero (also called delivery of a ghost pulse), the state machine of the circuitry determines that a stimulation signal was delivered, even though no actual stimulation signal was delivered, and transitions the control electrode circuitry to the passive recharge state so that the sensing circuitry can be calibrated in the correct state.

FIG. 1 is a conceptual diagram illustrating an example system 100 that includes an IMD 110 according to the techniques of the disclosure. Although the techniques described in this disclosure are generally applicable to a variety of medical devices including external devices and IMDs, application of such techniques to IMDs and, more particularly, implantable electrical stimulators (e.g., neurostimulators) will be described for purposes of illustration. More particularly, the disclosure will refer to an implantable SCS system for purposes of illustration, but without limitation as to other types of medical devices or other therapeutic applications of medical devices.

As shown in FIG. 1, system 100 includes an IMD 110, leads 108A and 108B, and external programmer 150 shown in conjunction with a patient 102, who is ordinarily a human patient. In the example of FIG. 1, IMD 110 is an implantable electrical stimulator that is configured to generate and deliver electrical stimulation therapy to patient 102 via one or more electrodes of electrodes 132A and/or 132B (collectively, "electrodes 132") of leads 108A and/or 108B (collectively, "leads 108"), e.g., for relief of chronic pain or other symptoms. In other examples, IMD 110 may be coupled to a single lead carrying multiple electrodes or more than two leads each carrying multiple electrodes. In some examples, the stimulation signals, or pulses (e.g., control pulses), may be configured to elicit detectable ECAP signals that IMD 110 may use to determine the posture state occupied by patient 102 and/or determine how to adjust one or more parameters that define stimulation therapy. The control pulses may provide therapeutic effect, but in one or more examples, the control pulses may not provide therapeutic effect. IMD 110 may be configured to delivered informed pulses for providing therapeutic effect. The informed pulses may be "informed" because the parameters of the informed pulses may be based on the ECAP signal generated from the delivery of control pulses. The informed pulses may be considered as providing governed therapy. Governed therapy may indicate that the stimulation pulses are for effective therapy. The control pulses may be "control" because the delivery of the control pulses is used to control the parameters for the informed pulses.

IMD 110 may be a chronic electrical stimulator that remains implanted within patient 102 for weeks, months, or even years. In other examples, IMD 110 may be a temporary, or trial, stimulator used to screen or evaluate the efficacy of electrical stimulation for chronic therapy. In one example, IMD 110 is implanted within patient 102. In some examples, a medical device, configured to perform techniques similar to IMD 110, may be an external device coupled to percutaneously implanted leads. In some examples, IMD 110 uses one or more leads, while in other examples, IMD 110 is leadless.

IMD 110 may be constructed of any polymer, metal, or composite material sufficient to house the components of IMD 110 (e.g., components illustrated in FIG. 2) within patient 102. In this example, IMD 110 may be constructed with a biocompatible housing, such as titanium or stainless steel, or a polymeric material such as silicone, polyurethane, or a liquid crystal polymer, and surgically implanted at a site in patient 102 near the pelvis, abdomen, or buttocks. In other examples, IMD 110 may be implanted within other suitable sites within patient 102, which may depend, for example, on the target site within patient 102 for the delivery of electrical stimulation therapy. The outer housing of IMD 110 may be configured to provide a hermetic seal for components, such as a rechargeable or non-rechargeable power source. In addition, in some examples, the outer housing of IMD 110 is selected from a material that facilitates receiving energy to charge the rechargeable power source.

Electrical stimulation energy, which may be constant current or constant voltage-based pulses, for example, is delivered from IMD 110 to one or more target tissue sites of patient 102 via one or more electrodes 132 of implantable leads 108. In the example of FIG. 1, leads 108 carry electrodes 132 that are placed adjacent to the target tissue of spinal cord 106. One or more of electrodes 132 may be disposed at a distal tip of a lead 108 and/or at other positions at intermediate points along the lead. Leads 108 may be implanted and coupled to IMD 110. Electrodes 132 may transfer electrical stimulation generated by an electrical stimulation generator in IMD 110 to tissue of patient 102. Although leads 108 may each be a single lead, lead 108 may include a lead extension or other segments that may aid in implantation or positioning of lead 108. In some examples, IMD 110 may be a leadless stimulator with one or more arrays of electrodes arranged on a housing of the stimulator rather than leads that extend from the housing. In addition, in some examples, system 100 may include one lead or more than two leads, each coupled to IMD 110 and directed to similar or different target tissue sites.

Electrodes 132 of leads 108 may be electrode pads on a paddle lead, circular (e.g., ring) electrodes surrounding the body of the lead, conformable electrodes, cuff electrodes, segmented electrodes (e.g., electrodes disposed at different circumferential positions around the lead instead of a continuous ring electrode), any combination thereof (e.g., ring electrodes and segmented electrodes) or any other type of electrodes capable of forming unipolar, bipolar or multipolar electrode combinations for therapy. Ring electrodes arranged at different axial positions at the distal ends of lead 108 will be described for purposes of illustration.

The deployment of electrodes 132 via leads 108 is described for purposes of illustration, but arrays of electrodes 132 may be deployed in different ways. For example, a housing associated with a leadless stimulator may carry arrays of electrodes 132, e.g., rows and/or columns (or other patterns), to which shifting operations may be applied. Such electrodes 132 may be arranged as surface electrodes, ring electrodes, or protrusions. As a further alternative, electrode arrays may be formed by rows and/or columns of electrodes 132 on one or more paddle leads. In some examples, electrode arrays include electrode segments, which are arranged at respective positions around a periphery of a lead, e.g., arranged in the form of one or more segmented rings around a circumference of a cylindrical lead. In other examples, one or more of leads 108 are linear leads having 8 ring electrodes along the axial length of the lead. In another example, electrodes 132 are segmented rings arranged in a linear fashion along the axial length of the lead and at the periphery of the lead.

The stimulation parameter set of a stimulation program that defines the stimulation pulses of electrical stimulation therapy by IMD 110 through the electrodes of leads 108 may include information identifying which electrodes 132 have been selected for delivery of stimulation according to a stimulation program, the polarities of the selected electrodes 132, i.e., the electrode combination for the program, voltage or current amplitude, pulse frequency, pulse width, pulse shape of stimulation delivered by electrodes 132. These stimulation parameters values that make up the stimulation parameter set that defines pulses may be predetermined parameter values defined by a user and/or automatically determined by system 100 based on one or more factors or user input. Informed pulses may be defined by a set of informed stimulation parameter values and control pulses may be defined by a set of control stimulation parameter values.

Although FIG. 1 is directed to SCS therapy, e.g., used to treat pain, in other examples system 100 may be configured to treat any other condition that may benefit from electrical stimulation therapy. In some examples, system 100 may be configured to provide multimodal stimulation using prime stimulation and base stimulation together. In some examples, system 100 may be used to treat tremor, Parkinson's disease, epilepsy, a pelvic floor disorder (e.g., urinary incontinence or other bladder dysfunction, fecal incontinence, pelvic pain, bowel dysfunction, or sexual dysfunction), obesity, gastroparesis, or psychiatric disorders (e.g., depression, mania, obsessive compulsive disorder, anxiety disorders, and the like). In this manner, system 100 may be configured to provide therapy taking the form of deep brain stimulation (DB S), peripheral nerve stimulation (PNS), peripheral nerve field stimulation (PNFS), cortical stimulation (CS), pelvic floor stimulation, gastrointestinal stimulation, or any other stimulation therapy capable of treating a condition of patient 102.

In some examples, lead 108 includes one or more sensors configured to allow IMD 110 to monitor one or more parameters of patient 102, such as patient activity, pressure, temperature, or other characteristics. The one or more sensors may be provided in addition to, or in place of, therapy delivery by lead 108. Rather than or in addition to lead 108 including such sensors, IMD 110 may include such sensors.

IMD 110 is generally configured to deliver electrical stimulation therapy (e.g., informed pulses and/or control pulses in the form of a prime pulse train and base pulse train, respectively) to patient 102 via selected combinations of electrodes 132 carried by one or both of leads 108, alone or in combination with an electrode carried by or defined by an outer housing of IMD 110. The target tissue for the electrical stimulation therapy may be any tissue affected by electrical stimulation, which may be in the form of electrical stimulation pulses or continuous waveforms. In some examples, the target tissue includes nerves, smooth muscle, or skeletal muscle. In the example illustrated by FIG. 1, the target tissue is tissue proximate spinal cord 106, such as within an intrathecal space or epidural space of spinal cord 106, or, in some examples, adjacent nerves that branch off spinal cord 106.

Leads 108 may be introduced into spinal cord 106 in via any suitable region, such as the thoracic, cervical, or lumbar regions. Stimulation of spinal cord 106 may, for example, prevent pain signals from traveling through spinal cord 106 and to the brain of patient 102. Patient 102 may perceive the interruption of pain signals as a reduction in pain and, therefore, efficacious therapy results. In other examples, stimulation of spinal cord 106 may produce paresthesia which may be reduce the perception of pain by patient 102, and thus, provide efficacious therapy results. In some examples, stimulation of spinal cord 106 or other anatomical structures associated with the spinal cord (e.g., nerves and cells associated with the nervous system) may provide relief from symptoms that may not produce paresthesia. For example, IMD 110 may deliver stimulation with intensities (e.g., values of amplitude and/or pulse width) below a sensory or perception threshold (e.g., sub-threshold stimulation) that reduces pain without paresthesia. In multimodal stimulation, for example, IMD 110 may deliver one pulse train at a higher frequency via one electrode combination and a second pulse train on an interleaved basis with a lower frequency via a second electrode combination, where both pulse trains are delivered at a sub-threshold intensity.

IMD 110 is configured to generate and deliver electrical stimulation therapy to a target stimulation site within patient 102 via electrodes 132 of leads 108 to patient 102 according to one or more therapy stimulation programs. A therapy stimulation program may generally define informed pulses, but may also define control pulses if the control pulses also contribute to a therapeutic effect. A therapy stimulation program defines values for one or more parameters (e.g., a parameter set) that define an aspect of the therapy delivered by IMD 110 according to that program. For example, a therapy stimulation program that controls delivery of stimulation by IMD 110 in the form of pulses may define values for voltage or current pulse amplitude, pulse width, pulse rate (e.g., pulse frequency), electrode combination, pulse shape, etc. for stimulation pulses delivered by IMD 110 according to that program. In some examples, one or more therapy stimulation programs define multiple different pulse trains that have different parameter values (e.g., different pulse frequencies, amplitudes, pulse widths, and/or electrode combinations) but are delivered on an interleaved basis to together provide a therapy for the patient.

Furthermore, IMD 110 may be configured to deliver control stimulation to patient 102 via a combination of electrodes 132 of leads 108, alone or in combination with an electrode carried by or defined by an outer housing of IMD 110 in order to detect ECAP signals (e.g., control pulses and/or informed pulses). The tissue targeted by the stimulation may be the same or similar tissue targeted by the electrical stimulation therapy, but IMD 110 may deliver stimulation pulses for ECAP signal detection via the same, at least some of the same, or different electrodes of electrodes 132. Since control stimulation pulses can be delivered in an interleaved manner with informed pulses (e.g., when the pulses configured to contribute to therapy interfere with the detection of ECAP signals or pulse sweeps intended for posture state detection via ECAP signals do not correspond to pulses intended for therapy purposes), a clinician and/or user may select any desired electrode 132 combination for informed pulses (i.e., governed therapy). Like the electrical stimulation therapy, the control stimulation may be in the form of electrical stimulation pulses or continuous waveforms.

In one example, each control stimulation pulse may include a balanced, bi-phasic square pulse that employs an active recharge phase. However, in other examples, the control stimulation pulses may include a monophasic pulse followed by a passive recharge phase. In other examples, a control pulse may include an imbalanced bi-phasic portion and a passive recharge portion. Although not necessary, a bi-phasic control pulse may include an interphase interval between the positive and negative phase to promote propagation of the nerve impulse in response to the first phase of the bi-phasic pulse. The control stimulation may be delivered without interrupting the delivery of the electrical stimulation informed pulses, such as during the window between consecutive informed pulses. The control pulses may elicit an ECAP signal from the tissue, and IMD 110 may sense the ECAP signal via two or more electrodes 132 on leads 108. In cases where the control stimulation pulses are applied to spinal cord 106, the signal may be sensed by IMD 110 from spinal cord 106.

A user, such as a clinician or patient 102, may interact with a user interface of an external programmer 150 to program IMD 110. Programming of IMD 110 may refer generally to the generation and transfer of commands, programs, or other information to control the operation of IMD 110. In this manner, IMD 110 may receive the transferred commands and programs from external programmer 150 to control stimulation, such as stimulation pulses that provide electrical stimulation therapy. For example, external programmer 150 may transmit therapy stimulation programs, stimulation parameter adjustments, therapy stimulation program selections, posture states, user input, or other information to control the operation of IMD 110, e.g., by wireless telemetry or wired connection.

In some cases, external programmer 150 may be characterized as a physician or clinician programmer if it is primarily intended for use by a physician or clinician. In other cases, external programmer 150 may be characterized as a patient programmer if it is primarily intended for use by a patient. A patient programmer may be generally accessible to patient 102 and, in many cases, may be a portable device that may accompany patient 102 throughout the patient's daily routine. For example, a patient programmer may receive input from patient 102 when the patient wishes to terminate or change electrical stimulation therapy, or when a patient perceives stimulation being delivered. In general, a physician or clinician programmer may support selection and generation of programs by a clinician for use by IMD 110, whereas a patient programmer may support adjustment and selection of such programs by a patient during ordinary use. In other examples, external programmer 150 may include, or be part of, an external charging device that recharges a power source of IMD 110. In this manner, a user may program and charge IMD 110 using one device, or multiple devices.

As described herein, information may be transmitted between external programmer 150 and IMD 110. Therefore, IMD 110 and external programmer 150 may communicate via wireless communication using any techniques known in the art. Examples of communication techniques may include, for example, radiofrequency (RF) telemetry and inductive coupling, but other techniques are also contemplated. In some examples, external programmer 150 includes a communication head that may be placed proximate to the patient's body near the IMD 110 implant site to improve the quality or security of communication between IMD 110 and external programmer 150. Communication between external programmer 150 and IMD 110 may occur during power transmission or separate from power transmission.

In some examples, IMD 110, in response to commands from external programmer 150, delivers electrical stimulation therapy (e.g., informed pulses and/or control pulses) according to a plurality of therapy stimulation programs to a target tissue site of the spinal cord 106 of patient 102 via electrodes 132 on leads 108. In some examples, IMD 110 modifies therapy stimulation programs as therapy needs of patient 102 evolve over time. For example, the modification of the therapy stimulation programs may cause the adjustment of at least one parameter of the plurality of stimulation pulses. When patient 102 receives the same therapy for an extended period, the efficacy of the therapy may be reduced. In some cases, parameters of the plurality of stimulation pulses may be automatically updated.

Efficacy of electrical stimulation therapy may be indicated by one or more characteristics (e.g., an amplitude of or between one or more peaks or an area under the curve of one or more peaks) of an action potential that is evoked by a control pulse delivered by IMD 110 (i.e., a characteristic value of the ECAP signal). Electrical stimulation therapy delivery by leads 108 of IMD 110 may cause neurons within the target tissue to evoke a compound action potential that travels up and down the target tissue, eventually arriving at sensing electrodes of IMD 110 (e.g., electrodes of electrodes 132 that are assigned for sensing). For instance, stimulation may also elicit at least one ECAP signal, and ECAPs responsive to stimulation may also be a surrogate for the effectiveness of the therapy. The amount of action potentials (e.g., number of neurons propagating action potential signals) that are evoked may be based on the various parameters of electrical stimulation pulses such as amplitude, pulse width, frequency, pulse shape (e.g., slew rate at the beginning and/or end of the pulse), etc. The slew rate may define the rate of change of the voltage and/or current amplitude of the control pulse at the beginning and/or end of each control pulse or each phase within the pulse. For example, a very high slew rate indicates a steep or even near vertical edge of the pulse, and a low slew rate indicates a longer ramp up (or ramp down) in the amplitude of the control pulse. In some examples, these parameters contribute to an intensity of the electrical stimulation. In addition, a characteristic of the ECAP signal (e.g., an amplitude) may change based on the distance between the stimulation electrodes and the nerves subject to the electrical field produced by the delivered control pulses.

Some example techniques for adjusting stimulation parameter values for stimulation pulses (e.g., informed pulses and/or control pulses that may or may not contribute to therapy for the patient) are based on comparing the value of a characteristic of a measured ECAP signal to a target ECAP characteristic value. In response to delivering a control pulse defined by a set of stimulation parameter values, IMD 110, via two or more electrodes interposed on leads 108, senses electrical potentials of tissue of the spinal cord 106 of patient 102 to measure the electrical activity of the tissue. IMD 110 senses ECAPs from the target tissue of patient 102, e.g., with electrodes on one or more leads 108 and associated sense circuitry. In some examples, IMD 110 receives a signal indicative of the ECAP from one or more sensors, e.g., one or more electrodes and circuitry, internal or external to patient 102. Such an example signal may include a signal indicating an ECAP of the tissue of patient 102. Examples of the one or more sensors include one or more sensors configured to measure a compound action potential of patient 102, or a physiological effect indicative of a compound action potential. For example, to measure a physiological effect of a compound action potential, the one or more sensors may be an accelerometer, a pressure sensor, a bending sensor, a sensor configured to detect a posture of patient 102, or a sensor configured to detect a respiratory function of patient 102. However, in other examples, external programmer 150 receives a signal indicating a compound action potential in the target tissue of patient 102 and transmits a notification to IMD 110.

In the example of FIG. 1, IMD 110 is described as performing a plurality of processing and computing functions. However, external programmer 150 instead may perform one, several, or all of these functions. Similarly, in some examples of this disclosure, processing circuitry of IMD 110 is described as performing a plurality of functions. However, processing circuitry of external programmer 150 may perform one, several, or all of these functions. In this alternative example, IMD 110 functions to relay sensed signals to external programmer 150 for analysis, and external programmer 150 transmits instructions to IMD 110 to adjust the one or more parameters defining the electrical stimulation therapy based on analysis of the sensed signals. For example, IMD 110 may relay the sensed signal indicative of an ECAP to external programmer 150. External programmer 150 may compare the parameter value of the ECAP to the target ECAP characteristic value, and in response to the comparison, external programmer 150 may instruct IMD 110 to adjust one or more stimulation parameter that defines the electrical stimulation informed pulses and, in some examples, control pulses, delivered to patient 102.

In some examples, the system changes the target ECAP characteristic value and/or growth rate(s) over a period of time, such as according to a change to a stimulation threshold (e.g., a perception threshold or detection threshold specific for the patient). The system may be programmed to change the target ECAP characteristic in order to adjust the intensity of informed pulses (i.e., governed therapy) to provide varying sensations to the patient (e.g., increase or decrease the volume of neural activation). Although the system may change the target ECAP characteristic value, received ECAP signals may still be used by the system to adjust one or more parameter values of the informed pulses and/or control pulses in order to meet the target ECAP characteristic value.

One or more devices within system 100, such as IMD 110 and/or external programmer 150, may perform various functions as described herein. For example, IMD 110 may include stimulation circuitry configured to deliver electrical stimulation, sensing circuitry configured to sense a plurality ECAP signals, and processing circuitry. The processing circuitry may be configured to control the stimulation circuitry to deliver a plurality of electrical stimulation pulses (e.g., control pulses) having different amplitude values and control the sensing circuitry to detect, after delivery of each electrical stimulation pulse of the plurality of electrical stimulation pulses, a respective ECAP signal of the plurality of ECAP signals.

In some examples described herein, reference may be made to one or more electrodes of IMD 110 "delivering" therapy. In these instances, it should be understood that stimulation circuitry of IMD 110 may be connected to the one or more electrodes and configured to deliver the therapy "using" or "on" the one or more electrodes. In some examples described herein, reference may be made to one or more electrodes of IMD 110 "sensing" ECAP signals. In these instances, it should be understood that sensing circuitry of IMD 110 may be connected to one or more electrodes and configured to sense the ECAP signals "using" or "on" the one or more electrodes. In some examples described herein, reference may be made to certain recharge states "on" one or more electrodes of IMD 110. In these instances, it should be understood that circuitry connected to the one or more electrodes may be "in" the certain recharge state.

IMD 110 may include a plurality of electrodes, wherein each electrode of the plurality of electrodes is configured to act as a stimulation electrode (e.g., to deliver governed therapy and/or control pulses when coupled to stimulation circuitry) and as a sensing electrode (e.g., to sense the ECAP signals when coupled to sensing circuitry). Each electrode of the plurality of electrodes may be couplable to the stimulation circuitry and the sensing circuitry. Processing circuitry may select a first set of one or more electrodes to couple to stimulation circuitry to act as the stimulation electrodes and a second set of one or more electrodes to couple to the sensing circuitry to act as the sensing electrodes.

In the example of FIG. 1, IMD 110 is described as performing a plurality of processing and computing functions. However, external programmer 150 instead may perform one, several, or all of these functions. In this alternative example, IMD 110 functions to relay sensed signals to external programmer 150 for analysis, and external programmer 150 transmits instructions to IMD 110 to adjust the one or more parameters defining the electrical stimulation signal based on analysis of the sensed signals. For example, IMD 110 may relay the sensed signal indicative of an ECAP to external programmer 150. External programmer 150 may compare the parameter value of the ECAP to the target ECAP characteristic value, and in response to the comparison, external programmer 150 may instruct IMD 110 to adjust one or more parameters that define the electrical stimulation signal.

Although electrical stimulation is generally described herein in the form of electrical stimulation pulses, electrical stimulation may be delivered in non-pulse form in other examples. For example, electrical stimulation may be delivered as a signal having various waveform shapes, frequencies, and amplitudes. Therefore, electrical stimulation in the form of a non-pulse signal may be a continuous signal that may have a sinusoidal waveform or other continuous waveform.

In some examples, sensing circuitry of IMD 110 may be coupled to sensing electrodes of electrodes 132. The sensing circuitry may include an operational amplifier configured to amplify ECAP signals within the circuitry for more accurate sensing of the ECAP signals. In some examples, stimulation circuitry of IMD 110 may be coupled to stimulation electrodes (e.g., control electrodes and/or governing electrodes) of electrodes 132. The stimulation electrodes may be configured to deliver control pulses to patient tissue that elicit ECAP signals from the tissue of patient 102, and may be referred to as control electrodes. The stimulation electrodes may be configured to deliver governed therapy (i.e., informed pulses) to patient tissue that provide therapy to patient 102, and may be referred to as governing electrodes. In some examples, the control electrodes and the governing electrodes are each a separate set of one or more electrodes. In some examples, the control electrodes and the governing electrodes are the same set of one or more electrodes.

Processing circuitry may be configured to enter an active recharge state on the stimulation electrodes (e.g., on the stimulation electrode circuitry) and, subsequent to entering the active recharge state, enter a passive recharge state on the stimulation electrodes. The active and passive recharge states are explained with more specificity below with reference to FIGS. 4-6. The processing circuitry may also be configured to calibrate, or auto-zero the operational amplifier of sensing circuitry while the control electrodes are in the passive recharge state. Processing circuitry may auto-zero the operational amplifier after the governing electrodes deliver a governed therapy (i.e., an informed pulse) and before the control electrodes deliver a control pulse.

Figure 2:
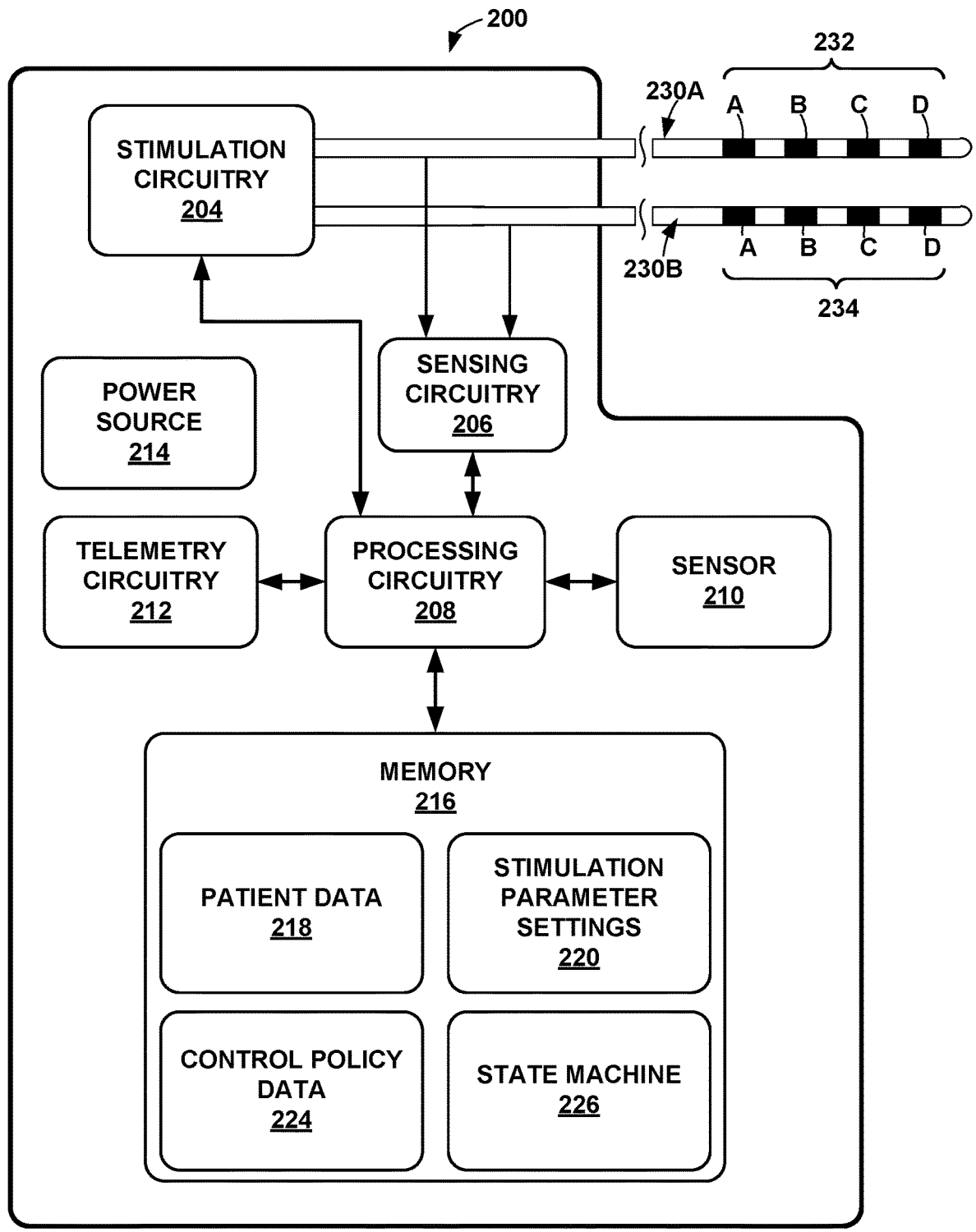
FIG. 2 is a block diagram of the example IMD of FIG. 1.

FIG. 2 is a block diagram of the example IMD of FIG. 1. IMD 200 may be an example of IMD 110 of FIG. 1. In the example shown in FIG. 2, IMD 200 includes stimulation circuitry 204, sensing circuitry 206, processing circuitry 208, sensor 210, telemetry circuitry 212, power source 214, and memory 216. Each of these circuits may be or include programmable or fixed function circuitry that can perform the functions attributed to respective circuitry. For example, processing circuitry 208 may include fixed-function or programmable circuitry, stimulation circuitry 204 may include circuitry for generating electrical stimulation signals such as pulses or continuous waveforms on one or more channels, sensing circuitry 206 may include sensing circuitry for sensing signals, and telemetry circuitry 212 may include telemetry circuitry for transmission and reception of signals. Memory 216 may store computer-readable instructions that, when executed by processing circuitry 208, cause IMD 200 to perform various functions described herein. Memory 216 may be a storage device or other non-transitory medium.

In the example shown in FIG. 2, memory 216 stores patient data 218, which may include anything related to the patient such as one or more patient postures, an activity level, or a combination of patient posture and activity level. Memory 216 may store stimulation parameter settings 220 within memory 216 or separate areas within memory 216. Each stored stimulation parameter setting 220 defines values for one or more sets of electrical stimulation parameters (e.g., an informed stimulation parameter set and a control stimulation parameter set, or parameters for other pulse trains). Stimulation parameter settings 220 may also include additional information such as instructions regarding delivery of electrical stimulation signals based on stimulation parameter relationship data, which can include relationships between two or more stimulation parameters based upon data from electrical stimulation signals delivered to patient 102 or data transmitted from external programmer 104. The stimulation parameter relationship data may include measurable aspects associated with stimulation, such as an ECAP characteristic value.

Memory 216 may also control policy data 224 in separate areas from or as part of patient stimulation parameter settings 220. Control policy data 224 may include instructions that processing circuitry 208 uses for delivering zero-amplitude pulses on control electrodes of IMD 200, as well as for calibrating sensing circuitry 206 of IMD 200, as described in more detail below. Memory 216 may include gain values that processing circuitry 208 may use to modulate informed and/or control stimulation pulses.

Memory 216 may also store a state machine 226. State machine 226 may define an order in which certain operations may be carried out within circuitry of IMD 200. For example, state machine 226 may define an order for different states of stimulation circuitry 204, sensing circuitry 206, and/or circuitry of electrodes 230. In some examples, state machine 226 may require that a stimulation therapy is delivered on one or more of electrodes 230 before the circuitry of the one or more of electrodes 230 may enter an active and/or passive recharge state.

Accordingly, in some examples, stimulation circuitry 204 generates electrical stimulation signals (e.g., informed pulses and control pulses) in accordance with the electrical stimulation parameters noted above. Other ranges of stimulation parameter values may also be useful and may depend on the target stimulation site within patient 102. While stimulation pulses are described, stimulation signals may be of any form, such as continuous-time signals (e.g., sine waves) or the like.

Sensing circuitry 206 may be configured to monitor signals from any combination of electrodes 232, 234. In some examples, sensing circuitry 206 includes one or more amplifiers, filters, and analog-to-digital converters. Sensing circuitry 206 may be used to sense physiological signals, such as ECAPs. In some examples, sensing circuitry 206 detects ECAPs from a particular combination of electrodes 232, 234. In some cases, the particular combination of electrodes for sensing ECAPs includes different electrodes than a set of electrodes 232, 234 used to deliver control stimulation pulses and/or informed stimulation pulses. Alternatively, in other cases, the particular combination of electrodes used for sensing ECAPs includes at least one of the same electrodes as a set of electrodes used to deliver informed and/or control stimulation pulses to patient 102. Sensing circuitry 206 may provide signals to an analog-to-digital converter, for conversion into a digital signal for processing, analysis, storage, or output by processing circuitry 208.

Processing circuitry 208 may include any one or more of a microprocessor, a controller, a digital signal processor (DSP), an application specific integrated circuit (ASIC), a field-programmable gate array (FPGA), discrete logic circuitry, or any other processing circuitry can provide the functions attributed to processing circuitry 208 herein may be embodied as firmware, hardware, software, or any combination thereof. Processing circuitry 208 controls stimulation circuitry 204 to generate electrical stimulation signals according to stimulation parameter settings 220 stored in memory 216 to apply stimulation parameter values, such as pulse amplitude, pulse width, pulse frequency, and waveform shape of each of the electrical stimulation signals.

In the example shown in FIG. 2, the set of electrodes 232 includes electrodes 232A, 232B, 232C, and 232D, and the set of electrodes 234 includes electrodes 234A, 234B, 234C, and 234D. Although only eight electrodes 232, 234 are pictured, in some examples, electrodes 232, 234 may include any number of electrodes. In some examples, a single lead may include all electrodes 232 and 234 along a single axial length of the lead. Processing circuitry 208 also controls stimulation circuitry 204 to generate and apply the electrical stimulation signals to selected combinations of electrodes 232, 234. In some examples, stimulation circuitry 204 includes a switch circuit that may couple stimulation signals to selected conductors within leads 230, which, in turn, deliver the stimulation signals across selected electrodes 232, 234. Such a switch circuit may be a switch array, switch matrix, multiplexer, or any other type of switch circuitry can selectively couple stimulation energy to selected electrodes 232, 234 and to selectively sense bioelectrical neural signals of a spinal cord of the patient (not shown in FIG. 2) with selected electrodes 232, 234.

In other examples, however, stimulation circuitry 204 does not include a switch circuit. In these examples, stimulation circuitry 204 comprises a plurality of pairs of voltage sources, current sources, voltage sinks, or current sinks connected to each of electrodes 232, 234 such that each pair of electrodes has a unique signal circuit. In other words, in these examples, each of electrodes 232, 234 is independently controlled via its own signal circuit (e.g., via a combination of a regulated voltage source and sink or regulated current source and sink), as opposed to switching signals between electrodes 232, 234.

Electrodes 232, 234 on respective leads 230 may be constructed of a variety of different designs. For example, one or both of leads 230 may include one or more electrodes at each longitudinal location along the length of the lead, such as one electrode at different perimeter locations around the perimeter of the lead at each of the locations A, B, C, and D. In one example, the electrodes may be electrically coupled to stimulation circuitry 204 via respective wires that are straight or coiled within the housing of the lead and run to a connector at the proximal end of the lead. In another example, each of the electrodes of the lead may be electrodes deposited on a thin film. The thin film may include an electrically conductive trace for each electrode that runs the length of the thin film to a proximal end connector. The thin film may then be wrapped (e.g., a helical wrap) around an internal member to form the lead 230. These and other constructions may be used to create a lead with a complex electrode geometry.

Although sensing circuitry 206 is incorporated into a common housing with stimulation circuitry 204 and processing circuitry 208 in FIG. 2, in other examples, sensing circuitry 206 may be in a separate housing from IMD 200 and may communicate with processing circuitry 208 via wired or wireless communication techniques.

In some examples, one or more of electrodes 232 and 234 may be suitable for sensing ECAPs. For instance, electrodes 232 and 234 may sense the voltage amplitude of a portion of the ECAP signals, where the sensed voltage amplitude is a characteristic the ECAP signal.

Memory 216 may be configured to store information within IMD 200 during operation. Memory 216 may include a computer-readable storage medium or computer-readable storage device. In some examples, memory 216 includes one or more of a short-term memory or a long-term memory. Memory 216 may include, for example, random access memories (RAM), dynamic random-access memories (DRAM), static random-access memories (SRAM), ferroelectric random-access memories (FRAM), magnetic discs, optical discs, flash memories, or forms of electrically programmable memories (EPROM) or electrically erasable and programmable memories (EEPROM). In some examples, memory 216 is used to store data indicative of instructions for execution by processing circuitry 208. As discussed herein, memory 216 can store patient data 218, stimulation parameter settings 220, and control policy data 224.

Sensor 210 may include one or more sensing elements that sense values of a respective patient parameter. As described, electrodes 232 and 234 may be the electrodes that sense, via sensing circuitry 206, a value of the ECAP indicative of a target stimulation intensity at least partially caused by a set of control stimulation parameter values. Sensor 210 may include one or more accelerometers, optical sensors, chemical sensors, temperature sensors, pressure sensors, or any other types of sensors. Sensor 210 may output patient parameter values that may be used as feedback to control delivery of electrical stimulation signals. IMD 200 may include additional sensors within the housing of IMD 200 and/or coupled via one of leads 108 or other leads. In addition, IMD 200 may receive sensor signals wirelessly from remote sensors via telemetry circuitry 212, for example. In some examples, one or more of these remote sensors may be external to patient (e.g., carried on the external surface of the skin, attached to clothing, or otherwise positioned external to the patient). In some examples, signals from sensor 210 may indicate a posture state (e.g., sleeping, awake, sitting, standing, or the like), and processing circuitry 208 may select target and/or threshold ECAP characteristic values according to the indicated posture state.

Telemetry circuitry 212 supports wireless communication between IMD 200 and an external programmer (not shown in FIG. 2) or another computing device under the control of processing circuitry 208. Processing circuitry 208 of IMD 200 may receive, as updates to programs, values for various stimulation parameters such as amplitude and electrode combination (e.g., for informed and/or control pulses), from the external programmer via telemetry circuitry 212. Updates to stimulation parameter settings 220 and input efficacy threshold settings may be stored within memory 216. Telemetry circuitry 212 in IMD 200, as well as telemetry circuits in other devices and systems described herein, such as the external programmer, may accomplish communication by radiofrequency (RF) communication techniques. In addition, telemetry circuitry 212 may communicate with an external medical device programmer (not shown in FIG. 2) via proximal inductive interaction of IMD 200 with the external programmer. The external programmer may be one example of external programmer 104 of FIG. 1. Accordingly, telemetry circuitry 212 may send information to the external programmer on a continuous basis, at periodic intervals, or upon request from IMD 110 or the external programmer.

Power source 214 delivers operating power to various components of IMD 200. Power source 214 may include a rechargeable or non-rechargeable battery and a power generation circuit to produce the operating power. Recharging may be accomplished through proximal inductive interaction between an external charger and an inductive charging coil within IMD 200. In other examples, traditional primary cell batteries may be used. In some examples, processing circuitry 208 may monitor the remaining charge (e.g., voltage) of power source 214 and select stimulation parameter values that may deliver similarly effective therapy at lower power consumption levels when needed to extend the operating time of power source 214.

According to the techniques of the disclosure, stimulation circuitry 204 of IMD 200 receives, via telemetry circuitry 212, instructions to deliver electrical stimulation according to stimulation parameter settings 220 to a target tissue site of the spinal cord of the patient via a plurality of electrode combinations of electrodes 232, 234 of leads 230 and/or a housing of IMD 200. Each electrical stimulation signal may elicit an ECAP that is sensed by sensing circuitry 206 via electrodes 232 and 234. Processing circuitry 208 may receive, via an electrical signal sensed by sensing circuitry 206, information indicative of an ECAP signal (e.g., a numerical value indicating a characteristic of the ECAP in electrical units such as voltage or power) produced in response to the electrical stimulation signal(s). Stimulation parameter settings 220 may be updated according to the ECAPs recorded at sensing circuitry 206.

Figure 3:
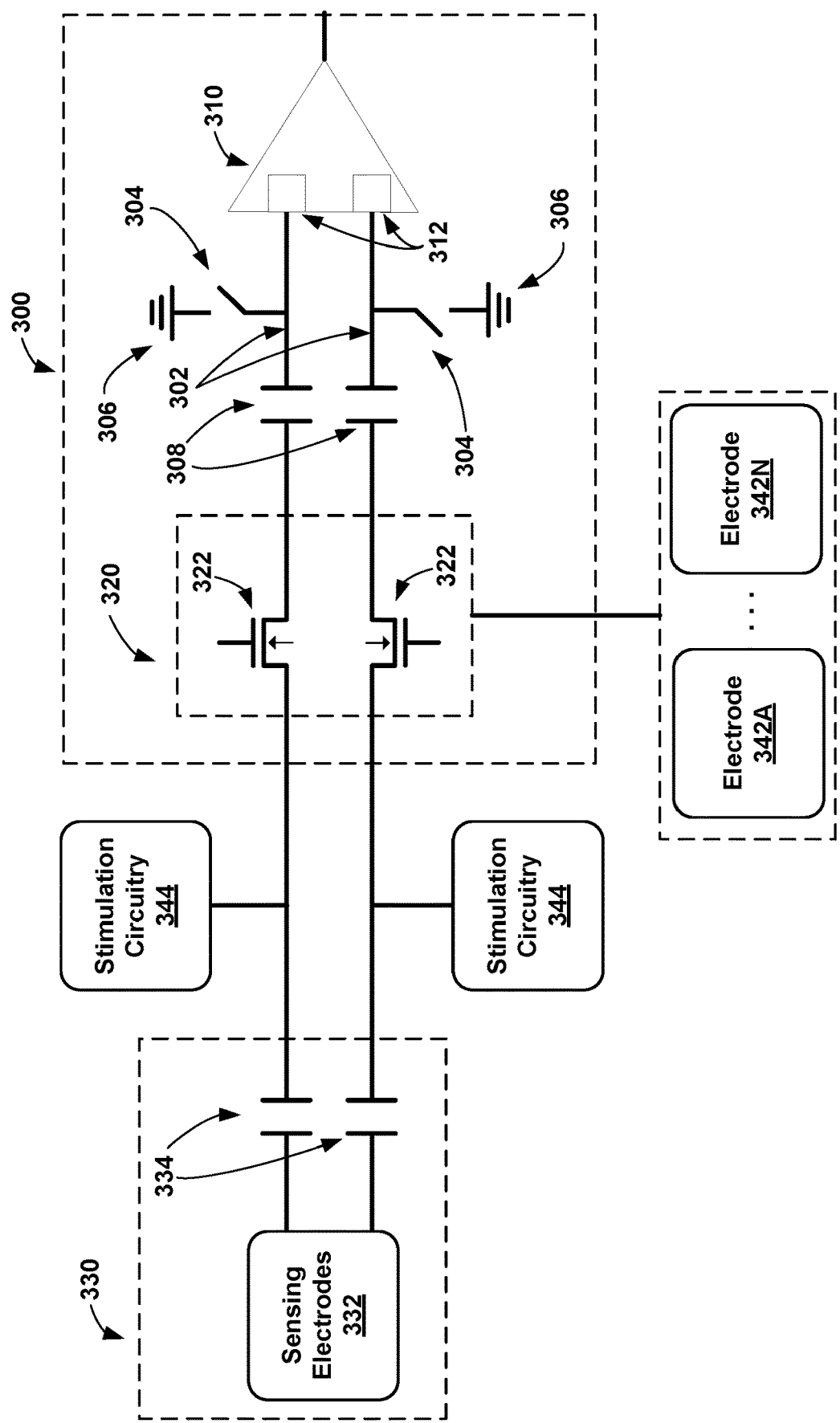
FIG. 3 is a conceptual diagram illustrating an example of sensing circuitry coupled to sensing electrodes according to the techniques of the disclosure.

FIG. 3 is a conceptual diagram illustrating an example of sensing circuitry 300 coupled to sensing electrodes 332 according to the techniques of the disclosure. Sensing circuitry 300 may be an example of a portion of sensing circuitry 206 of FIG. 2. As described, sensing circuitry 300 of the IMD may be configured to sense an ECAP signal from patient tissue. Sensing circuitry 300 may include an operational amplifier 310, where operational amplifier 310 is configured to amplify an ECAP signal sensed on sensing electrodes 332. Sensing circuitry 300 may include wires 302, coupling capacitors 334, calibration capacitors 308, one or more connections to IMD ground 306, one or more calibration switches 304, and a gate drive 320. Amplifier 310 may include inputs 312 where wires 302 connect to amplifier 310.

Sensing electrodes 332 may be examples of electrodes 232, 234 of FIG. 2 and may be coupled to sensing circuitry 300. Sensing circuitry 300 may be couplable to a plurality of electrodes, including electrodes 342 and sensing electrodes 332, through gate drive 320. Processing circuitry of the IMD (e.g., processing circuitry 208 of FIG. 2) may select any of the plurality of electrodes of the IMD to couple to the sensing circuitry to act as sensing electrodes 332. For example, selection switches 322 of gate drive 320 may be closed for one or more of the plurality of electrodes, allowing those electrodes to be used as sensing electrodes 332. Selection switches 322 of gate drive 320 may be open for all other electrodes 342 so that current in the circuitry of the other electrodes 342 does not interfere with sensing circuitry 300 as it senses for ECAP signals. Sensing electrodes 332 may be part of sensing electrode circuitry 330, including coupling capacitors 334. Coupling capacitors 334 may protect against DC current flowing into the body, resulting in tissue damage during therapy. Each electrode 342A-342N may be part of electrode circuitry that includes coupling capacitors.

In some examples, selection switches 322 of gate drive 320 may be Metal Oxide Semiconductor Field Effect Transistors (MOSFETs), N-type metal oxide semiconductors (NMOSs, which may be a type of MOSFET in which electrons are the dominant charge carrier in the semiconductor channel), or P-type metal oxide semiconductors (PMOS), being used as switches. References to "closing" or "opening" such switches may reference using a gate within the circuitry to control the conduction between two sides of the switch.

Sensing electrodes 332 may rest against the patient tissue (e.g., spinal cord) of a patient. One or more sensing electrodes 332 may collect an ECAP signal from patient tissue and provide an electrical signal to sensing circuitry 300 representing an amplitude of the ECAP signal. Amplifier 310 may amplify the ECAP signal to allow the IMD to more accurately sense and measure the ECAP signal. For ease of description, other components of sensing circuitry 300 are not shown in FIG. 3, and would appear to the right of amplifier 310 in FIG. 3.

Each electrode of the plurality of electrodes (e.g., electrodes 342 and sensing electrodes 332) may be couplable to stimulation circuitry 344. In some examples, stimulation circuitry 344 includes a switch circuit that may couple stimulation signals to selected conductors within the leads, which, in turn, deliver the stimulation signals across the selected electrodes. Such a switch circuit may be a switch array, switch matrix, multiplexer, or any other type of switch circuitry that can selectively couple stimulation energy to the selected electrodes. The switches in stimulation circuitry 344 to sensing electrodes 332 may be open so that current in stimulation circuitry 344 does not interfere with sensing electrodes' 332 ability to sense for ECAP signals. In some examples, however, stimulation circuitry 344 does not include a switch circuit. In these examples, stimulation circuitry 344 comprises a plurality of pairs of voltage sources, current sources, voltage sinks, or current sinks connected to each of electrodes 342 such that each pair of electrodes has a unique signal circuit. In other words, in these examples, each of electrodes 342 is independently controlled via its own signal circuit (e.g., via a combination of a regulated voltage source and sink or regulated current source and sink), as opposed to switching signals between electrodes 342. The voltage sources and sinks of stimulation circuitry 344 for sensing electrodes 332 may be off (e.g., "not coupled") so that no current in the stimulation circuitry 344 for sensing electrodes 332 interferes with sensing electrodes' 332 ability to sense for ECAP signals.

In some examples, stimulation circuitry may be coupled to one or more of the plurality of electrodes (e.g., one or more of electrodes 342) called the stimulation electrodes. Stimulation electrodes may be control electrodes configured to deliver control pulses and/or governing electrodes configured to deliver governed therapy. In some examples, the control electrodes and the governing electrodes are each a separate set of one or more electrodes. In some examples, the control electrodes and the governing electrodes are the same set of one or more electrodes.

While control electrode circuitry is in a passive recharge state, processing circuitry may auto-zero inputs 312 to the operational amplifier 310 of sensing circuitry 300. Inputs 312 may include an "A terminal" and a "B terminal." Auto-zeroing the inputs 312 to the operational amplifier 310 may calibrate the sensing circuitry 300 for sensing ECAP signals from patient tissue. As the IMD operates, charge may build up in wires 302 at calibration capacitors 308. To auto-zero the inputs 312 to the operational amplifier 310, processing circuitry may close calibration switches 304 to connect the inputs of operational amplifier 310 to IMD ground 306. Any offsets in wires 302 near the inputs 312 may be stored on calibration capacitors 308. For example, processing circuitry may connect a first input (e.g., terminal A) to the operational amplifier 310 to IMD ground 306 by closing a first switch of calibration switches 304. By connecting the first input to IMD ground 306, processing circuitry causes voltage offsets in a first wire of wires 302 of sensing circuitry 300 to be stored in a first capacitor of capacitors 308 on the first wire. In another example, processing circuitry may connect a second input (e.g., terminal B) to the operational amplifier 310 to IMD ground 306 by closing a second switch of calibration switches 304. By connecting the second input to IMD ground 306, processing circuitry causes voltage offsets in a second wire of wires 302 of sensing circuitry 300 to be stored in a second capacitor of capacitors 308 on the second wire.

To auto-zero the inputs 312 of operational amplifier 310, the processing circuitry may be configured to zero a differential signal between operational amplifier 310 inputs 312 and zero a common-mode signal on operational amplifier 310 inputs 312. A differential signal between inputs 312 may be calculated by determining a difference in voltage between the A terminal and B terminal of inputs 312. For example, if the input to terminal A is 100.25 millivolts and the input to terminal B is 99.75 millivolts, the differential signal would be 0.5 millivolts. By storing offsets on the calibration capacitors 308 as described above, the processing circuitry may ensure that a differential signal across terminals A and B of inputs 312 is low enough for operational amplifier to receive and amplify an accurate ECAP signal, because differences in the inputs to the A and B terminals would be stored on calibration capacitors 308. In some examples, the differential signal after auto-zeroing may be less than thirty microvolts.

A common mode signal on inputs 312 may be calculated by determining an average voltage across the A terminal and B terminal of inputs 312. For example, if the input to terminal A is 100.25 millivolts and the input to terminal B is 99.75 millivolts, the common mode signal would be 100 millivolts. By connecting the circuitry of sensing circuitry 300 to IMD ground (i.e., closing switches 322 and calibration switches 304 to connect coupling capacitors 334 and calibration capacitors 308 to IMD ground 306) the processing circuitry may ensure that the common mode offset to the inputs 312 of operational amplifier 310 is near zero, removing the common mode offset received from the patient tissue through sensing electrodes 332. Operational amplifier 310 may be designed to accept common mode input ranges based on known common mode input ranges of body tissue after the auto-zero operation. In some examples, the input range of operational amplifier may be around plus or minus 100 millivolts.

To be effectively calibrated, sensing circuitry 300 should be calibrated when the IMD circuitry is in the same state as when sensing circuitry 300 would be sensing an ECAP signal. The IMD may sense for ECAP signals when control electrode circuitry is in a state of passive recharge, e.g., after control electrodes of electrodes 342 deliver a control pulse configured to elicit the ECAP signal and while coupling capacitors of the control electrode circuitry are connected to one another in a circuit loop to eliminate stored charge on the coupling capacitors of the control electrode circuitry. For example, each coupling capacitor of the control electrode circuitry may be connected to IMD ground to form the circuit loop. In some examples, each coupling capacitor of the control electrode circuitry may be connected to a constant voltage source to form the loop. However, there may not be enough time between a control pulse and the subsequent ECAP signal for the processing circuitry of the IMD to calibrate sensing circuitry 300. Therefore, the processing circuitry should calibrate sensing circuitry 300 at another time when control electrode circuitry is in a passive recharge state. In order to auto-zero the inputs 312 to operational amplifier 310, the processing circuitry may be configured to auto-zero the inputs 312 while control electrode circuitry is in the passive recharge state before the control electrodes deliver a control pulse to patient tissue.

The stimulation electrode circuitry may be programmed to automatically enter different recharge states following the delivery of different pulses. That is, an internal state machine of the IMD circuitry may be configured to transition stimulation electrode circuitry (e.g., governing electrode circuitry, control electrode circuitry) to an active or passive recharge state after stimulation is delivered on the stimulation electrodes (e.g., governing electrodes, control electrodes). For example, the governing electrode circuitry may be programmed to automatically enter active and passive recharge states following the delivery of an informed pulse (i.e., governed therapy). For another example, the processing circuitry may cause stimulation circuitry 344 to deliver, on the control electrodes, electrical stimulation therapy to a patient. The electrical stimulation therapy may include a control pulse configured to elicit an ECAP response from patient tissue, or a ghost pulse (e.g., an electrical stimulation signal having an amplitude substantially equal to zero) configured to induce an intended internal state of the IMD circuitry. For example, after delivery of a control pulse on the control electrodes, the control electrode circuitry may automatically enter an active recharge state, followed by a passive recharge state. Sensing circuitry may sense for an ECAP while the control electrodes are in the passive recharge state following the delivery of the control pulse.

In some examples, the control electrode circuitry may automatically enter the passive recharge state after being instructed to deliver a ghost pulse. In some examples, the ghost pulse may be a zero-milliamp pulse (i.e., a zero-milliamp electrical stimulation therapy). For purposes of calibration, no stimulation signal is needed, but the state machine of the circuitry may need to first have a stimulation pulse that is delivered before the state machine can transition to the intended recharge state. Accordingly, by instructing the stimulation circuitry to deliver a ghost pulse on the control electrodes, the state machine of the circuitry may determine that a stimulation signal was delivered, even though no actual stimulation signal was delivered, and transitions to the intended recharge state so that the sensing circuitry can be calibrated in the correct state. For example, after delivery of a ghost pulse on the control electrodes, the control electrode circuitry may automatically enter an active recharge state, followed by a passive recharge state. In some examples, the control electrode circuitry may automatically enter the passive recharge state following the delivery of the ghost pulse. The processing circuitry may auto-zero inputs 312 to operational amplifier 310 of sensing circuitry 300 of the IMD while the control electrode circuitry is in the passive recharge state following the ghost pulse.

The IMD may be configured to perform therapy on patient tissue according to a cycle. For example, the processing circuitry of the IMD may cause stimulation circuitry 344 to deliver, on governing electrodes, a governed therapy to the patient after sensing for the evoked compound action potential. After delivery of the governed therapy, the processing circuitry may enter the governing electrode circuitry into a passive recharge state on the governing electrodes. In some examples, processing circuitry may also enter the governing electrode circuitry into an active recharge state following an informed pulse and before a passive recharge state and/or another informed pulse. While the governing electrode circuitry is in a passive recharge state, and in order to elicit an active recharge state on the control electrode circuitry, processing circuitry may be further configured to instruct stimulation circuitry of the medical device to deliver, on the control electrodes, an electrical stimulation signal having an amplitude substantially equal to zero to the patient (e.g., a ghost pulse). The ghost pulse may induce the state machine of the IMD circuitry to enter an intended recharge state for calibration. For example, following the ghost pulse, processing circuitry may be configured to enter the control electrode circuitry into a first active recharge state, and, subsequent to entering the first active recharge state, enter a first passive recharge state on the control electrode circuitry. Because the ghost pulse has an amplitude substantially equal to zero, the current source of the circuit during the first active recharge state may apply a "zero-milliamp" current through the circuit, in effect not applying a current at all, and thus effectively not performing an active recharge. In some examples, following the ghost pulse, the processing circuitry may enter the control electrode circuitry into the first passive recharge state. While the control electrode circuitry is in the first passive recharge state, the processing circuitry may be configured to calibrate sensing circuitry 300. Thus, the processing circuitry may be configured to auto-zero inputs 312 to operational amplifier 310 after stimulation circuitry 344 delivers a governed therapy on the governing electrodes and before stimulation circuitry delivers a control pulse on the control electrodes, for example, during the first passive recharge state on the control electrodes. By auto-zeroing inputs 312 to operational amplifier 310, the processing circuitry may discharge the charge on calibration capacitors 308, effectively zeroing a differential signal and common-mode signal on operational amplifier 310 inputs 312. After the first passive recharge state on the control electrodes, the processing circuitry may cause stimulation circuitry 344 to deliver, on the control electrodes, electrical stimulation therapy to a patient, the electrical stimulation therapy comprising the control pulse. The control pulse may be followed by a second active recharge state on the control electrode circuitry (e.g., following the control pulse, processing circuitry may be configured to enter the control electrode circuitry into a second active recharge state), and the second active recharge state may be followed by a second passive recharge state on the control electrode circuitry (e.g., following the second active recharge state, processing circuitry may be configured to enter the control electrode circuitry into a second passive recharge state). The processing circuitry may be configured to cause the sensing circuitry to sense, during the second passive recharge state, for an ECAP. Following sensing for an ECAP, the processing circuitry may cause stimulation circuitry 344 to deliver a governed therapy to the patient tissue on the governing electrodes. The cycle may then repeat. Although in the previous example the cycle started with delivery of a governed therapy, in some examples the cycle may begin at any step.

Instructions may be stored in a memory of the IMD directing the processing circuitry to enter stimulation electrode circuitry (e.g., governing electrode circuitry, control electrode circuitry) into the one or more recharge states following a pulse therapy delivered on the stimulation electrodes (e.g., governing electrodes, control electrodes).

Figure 4:
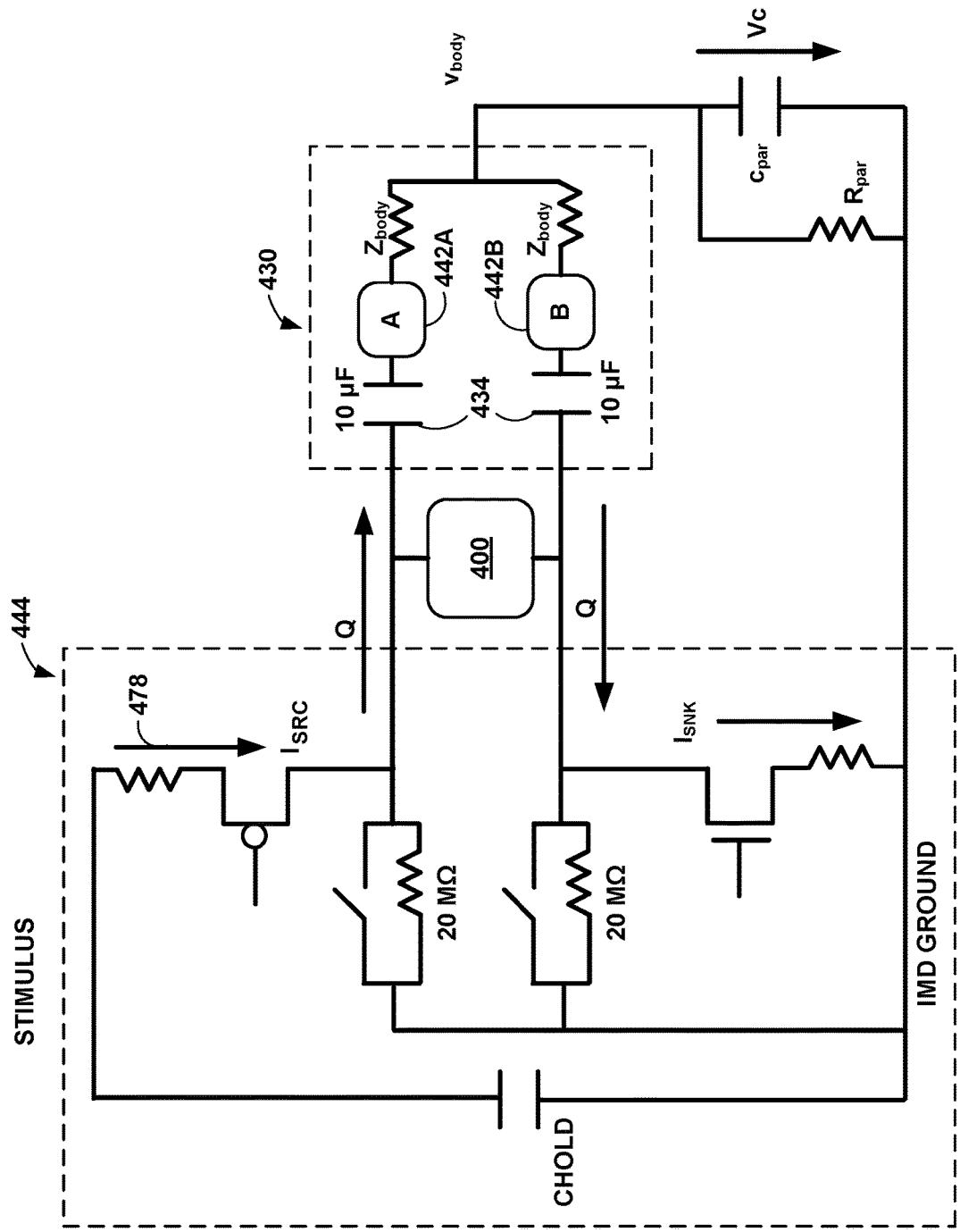
FIG. 4 is a conceptual diagram illustrating an example stimulus state of operation of a stimulation circuit, in accordance with one or more techniques of this disclosure.

FIG. 4 is a conceptual diagram illustrating an example stimulus state of operation of a stimulation circuit, in accordance with one or more techniques of this disclosure. The stimulus circuit may include stimulation circuitry 444 and stimulation electrode circuitry 430, including stimulation electrodes 442A and 442B. Although only two stimulation electrodes 442 are shown, stimulation electrodes 442 may include more than two electrodes. Stimulation circuitry 444 may be an example of part of stimulation circuitry 204 of FIG. 2 and/or stimulation circuitry 344 of FIG. 3. In some examples, stimulation electrodes 442 may be control electrodes configured to deliver control pulses. In some examples, stimulation electrodes 442 may be governing electrodes configured to deliver governed therapy. In some examples, stimulation electrodes 442 may act as both the control electrodes and the governing electrodes. Coupling capacitors 434 may protect against DC current flowing into the body, resulting in tissue damage during therapy.

The IMD may include a plurality of electrodes, where each electrode of the plurality is couplable to stimulation circuitry 444. When processing circuitry of the IMD selects one or more electrodes of the plurality to couple to stimulation circuitry 444, those may be referred to as stimulation electrodes 442. Each of the plurality of electrodes may be couplable to sensing circuitry 400 as well. When processing circuitry of the IMD selects one or more electrodes of the plurality to couple to sensing circuitry 400, those may be referred to as sensing electrodes. When stimulation electrodes 442 are coupled to stimulation circuitry 444, they may not be coupled to sensing circuitry 400. For example, one or more switches of sensing circuitry 400 may be open to stimulation electrodes 442 when stimulation electrodes 442 are not selected as sensing electrodes, to prevent current in the stimulation circuit from interfering with sensing circuitry 400. In some examples, the plurality of electrodes may be couplable to stimulation circuitry and/or sensing circuitry using one or more NMOS-based switches. The NMOS-based switches may remain closed to electrodes not "coupled" to one or more of the stimulation circuitry and the sensing circuitry, such that the NMOS-based switches act as voltage clamps, maintaining safe voltages for downstream circuitry. Sensing circuitry 400 may be an example of sensing circuitry 206 of FIG. 2 and/or sensing circuitry 300 of FIG. 3.

The stimulus hardware of the IMD may be used to establish the relative voltage between IMD ground and the common body voltage ($V_{body}$), which may be important to ECAP sensing. For example, stimulation circuitry 444 may include a current source ($I_{SRC}$) and a current sink ($I_{SNK}$) coupled to stimulation electrodes 442. In some examples, stimulation circuitry 444 may comprise a plurality of pairs of voltage sources, current sources, voltage sinks, or current sinks connected to each of the plurality of electrodes of the IMD such that each pair of electrodes has a unique signal circuit. In other words, each of electrodes 442 may be independently controlled via its own signal circuit (e.g., via a combination of a regulated voltage source and sink or regulated current source and sink). For example, to activate electrode 442A as a cathode, processing circuitry of the IMD may turn on a current source (e.g., $I_{SRC}$) that is connected to electrode 442A and specify an amount of electric current amplitude to be delivered with each pulse. To activate electrode 442B as an anode, the processing circuitry may turn on a current sink (e.g., $I_{SNK}$) connected to electrode 442B, which causes electrode 442B to sink the amount of current sourced by electrode 442A. The processing circuitry may time-multiplex different electrode combinations by turning on different sources and sinks, connected to different electrodes, at different times. Multi-electrode combinations of multiple cathodes and/or multiple anodes (e.g., one cathode and multiple anodes or one anode and multiple cathodes) may be formed by selectively turning on particular sources and sinks, with the total amount of current sourced by the current sources of the cathodes being nearly equal to the total amount of current sunk by the current sinks of the anode. In some examples, the IMD case may form an anode. The voltage sources and sinks for the one or more electrodes selected as sensing electrodes may be turned off to prevent current from interfering with sensing circuitry 400.

In the example of FIG. 4, stimulation circuitry 444 may apply current 478 over some time period, t, to deliver electrical stimulation therapy to patient tissue via electrodes 442. When a stimulus with charge Q is applied via current 478 (e.g., Q=current 478*t), the voltage across coupling capacitors 434 may change from an initial voltage (which may be nearly equal to zero, $V_0$) by some change in voltage ($\Delta V$), where $\Delta V$ may be approximately equal to the Q divided by the capacitance of coupling capacitors 434. That is, in some examples, $\Delta V \approx Q/10$ µF, and the voltage stored on coupling capacitor 434A may be approximately equal to $V_0 + \Delta V$ and the voltage stored on coupling capacitor 434B may be approximately equal to $V_0 - \Delta V$. In some examples, current 478 is a control pulse configured to elicit an ECAP signal from nerve tissue of the patient. In some examples, current 478 is a governed therapy configured to deliver therapy to the patient.

Figure 5:
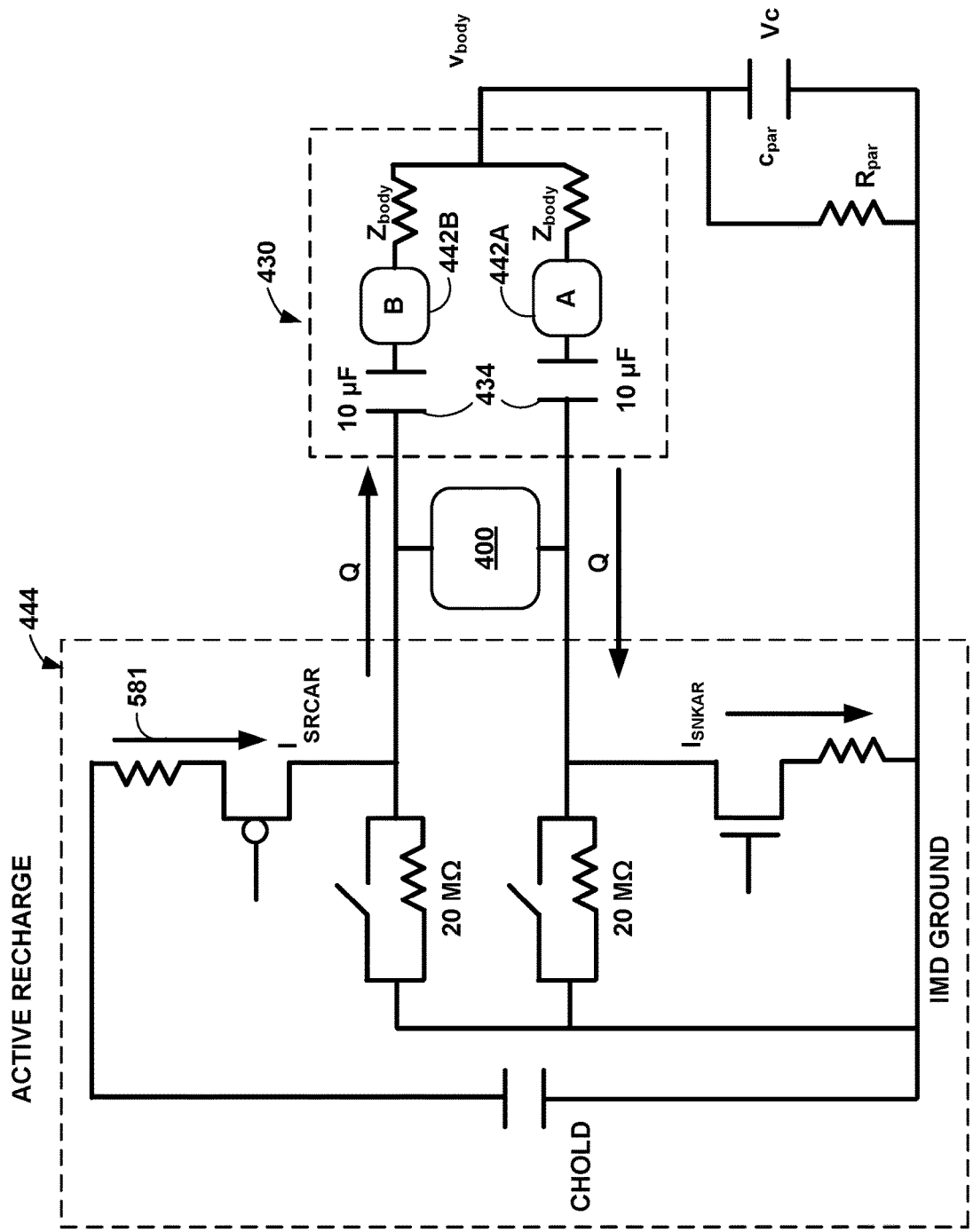
FIG. 5 is a conceptual diagram illustrating an example active recharge state of operation of the stimulation circuit of FIG. 4, in accordance with one or more techniques of this disclosure.
Figure 6:
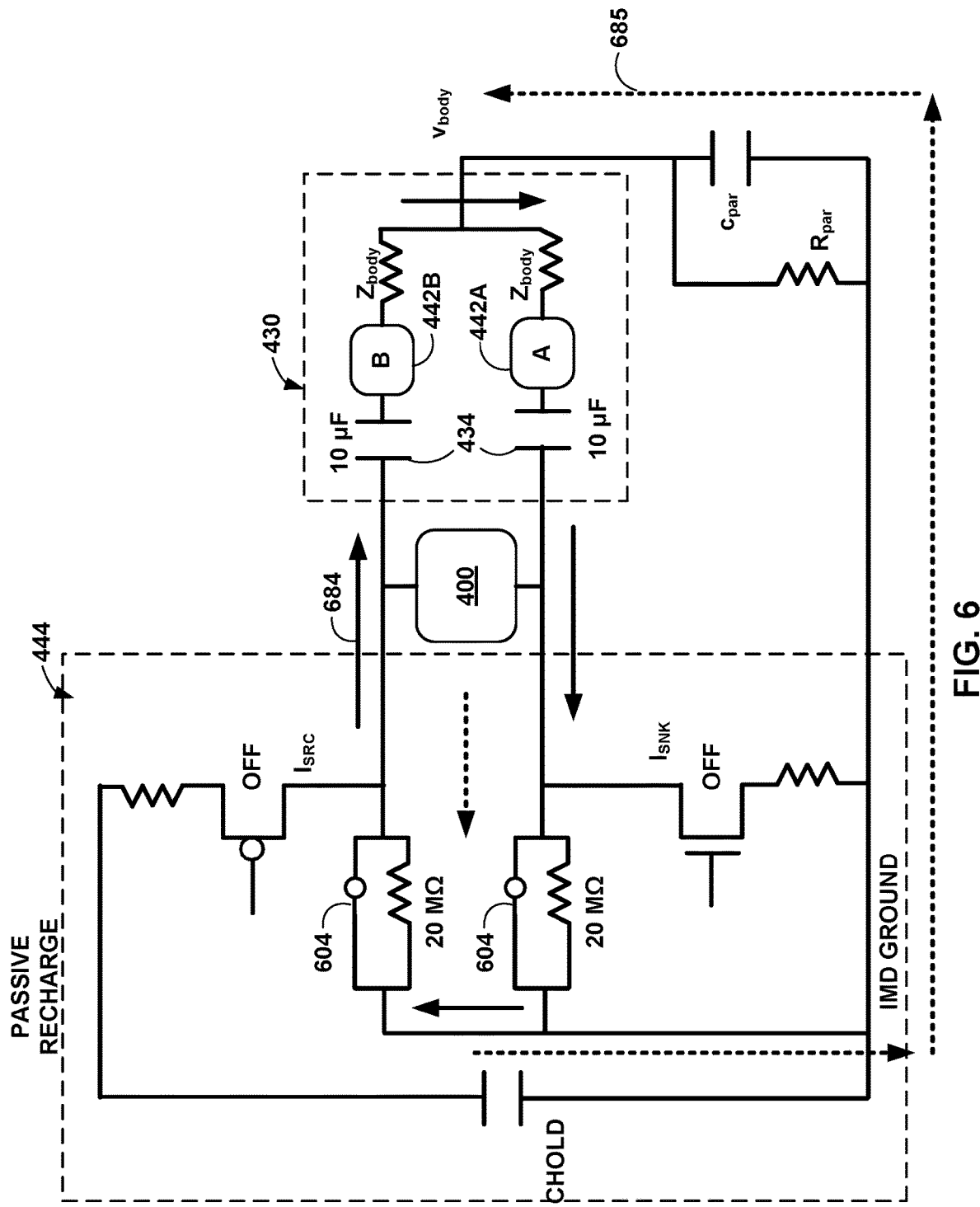
FIG. 6 is a conceptual diagram illustrating an example passive recharge state of operation in the stimulation circuit of FIG. 4, in accordance with one or more techniques of this disclosure.

In FIGS. 4-6, $Z_{body}$ represents the electrode body interface. The electrode body interface may be described as an ion double layer capacitor in parallel with an ion oxidation reduction pathway, which may be described by the Butler-Volmer equation. The ion double layer capacitor in parallel with the ion oxidation reduction pathway may be in series with an Ohmic body impedance. A further simplified model of the electrode body interface may be referred to as Randles circuit, which is a leaky capacitor in series with an ohmic body impedance.

In FIGS. 4-6, a parasitic resistance ($R_{par}$) and parasitic capacitance ($c_{par}$) is shown between $V_{body}$ and IMD ground. $R_{par}$ and $c_{par}$ may represent various leakages and passages between the body and the IMD ground through which current may flow, for example, through the casing of the IMD. $R_{par}$ and $c_{par}$ may represent a very high impedance, that is, $R_{par}$ may represent a very high resistance (e.g., greater than five Megaohms), and $c_{par}$ may represent a very small capacitance (e.g., less than ten nanofarads). Values for $R_{par}$ and $c_{par}$ may be experimentally determined, and may affect the voltage waveform between $V_{body}$ and IMD ground. In the example of FIG. 4, a voltage, $V_C$, may be stored on $c_{par}$ as a result of the stimulus.

In FIG. 4-6, the 20MΩ resistors and switches connected in parallel with them, may be connected instead to a constant positive voltage with respect to IMD ground, instead of IMD ground itself. This configuration may prevent the interior side of coupling capacitors 434 from being below IMD ground in certain modes of operation, unintentionally turning on electrostatic discharge (ESD) protection diodes and diodes to the silicon substrate. In some examples, this alternate configuration may be beneficial when there is residual charge on coupling capacitors 434 of stimulation electrodes 442, while another set of electrodes of the IMD is in a passive recharge state.

FIG. 5 is a conceptual diagram illustrating an example active recharge state of operation of the stimulation circuit of FIG. 4, in accordance with one or more techniques of this disclosure. As stimulation circuitry 444 delivers therapy to patient tissue, charge builds up in coupling capacitors 434. Coupling capacitors 434 prevent accumulated charge in IMD circuitry from impacting the patient. In order to relieve the accumulated charge on coupling capacitors, processing circuitry may cause stimulation circuitry 444 and stimulation electrode circuitry 430 to enter an active recharge state.

For example, processing circuitry may cause stimulation circuitry 444 to apply a voltage (e.g., via $I_{SRCAR}$ and $I_{SNKAR}$) to wires of stimulation electrode circuitry 430, where the voltage applied is opposite to a charge stored on coupling capacitors 434. For example, stimulation circuitry 444 may include a current source and a current sink as described above during a stimulus operation, where the current source is configured to send a first current having a first charge through coupling capacitors 434 and stimulation electrodes 442 to provide therapy to the patient. During active recharge, the current source and current sink may switch, and the new current source ($I_{SRCAR}$) may send a second current having the first charge through coupling capacitors 434 in the opposite direction to dissipate accumulated charge on coupling capacitors 434. In the example of FIG. 5, the current source and sink have switched between stimulation electrode 442A and 442B, as shown by the flipped location of stimulation electrodes 442A and 442B in the diagram. In the example of FIG. 5, stimulation circuitry 444 may apply current 581 over some time period, t, to perform an active recharge state operation. The current being applied to the patient may remove the charge on the 10 g coupling capacitors 434 that was added during stimulus, which may return coupling capacitors 434 to the initial voltage ($V_0$). For example, a charge Q may be applied via current 581 (e.g., Q=current 581*t) that is roughly equivalent to the charge applied during stimulus. The voltage across coupling capacitors 434 may change by the same change in voltage ($\Delta V$) as from the stimulus, but in the opposite direction. In some examples, $\Delta V \sim Q/10$ μF, and the voltage stored on coupling capacitor 434A may change from approximately $V_0 + \Delta V$ to approximately $V_0$, and the voltage stored on coupling capacitor 434B may change from approximately $V_0 - \Delta V$ to approximately $V_0$. In the example of FIG. 5, approximately a nominal voltage, $V_C$, may be stored, or remain stored, on $c_{par}$ as a result of the active recharge and/or previous stimulus. In some examples, the charge applied during stimulus is not exactly equal to the charge applied during active recharge, hence the voltages described above across the capacitors of the circuitry may only be approximate.

Stimulation electrode circuitry 430 may automatically enter an active recharge state following the delivery of a pulse (e.g., control pulse, governed therapy). For example, instructions may be stored in a memory of the IMD directing processing circuitry to enter one or more recharge states on stimulation electrode circuitry 430 following any pulse delivered by the stimulation electrodes 442. In some examples, a state machine may be implemented in the processing circuitry to automatically transition stimulation electrode circuitry 430 to different states following delivery of a pulse on stimulation electrodes 442.

For example, processing circuitry 208 may implement a state machine that defines an order in which stimulation electrode circuitry 430 enters various states like an active recharge state. One example of the criteria to enter an active recharge state may be for stimulation circuitry 444 to deliver electrical stimulation. However, in some cases, such as when sensing circuitry 400 is being calibrated, no stimulation signal is needed. Sensing circuitry 400 may be calibrated while control electrodes of stimulation electrodes 442 are in a passive recharge state. Although no stimulation signal is needed, the processing circuitry may not be configured to transition control electrode circuitry 430 to the active recharge state or the passive recharge state until the act of outputting a stimulation signal is performed. Accordingly, in some examples, the processing circuitry may instruct stimulation circuitry 444 to output an electrical stimulation signal having an amplitude substantially equal to zero (e.g., a ghost pulse) on the control electrodes. A ghost pulse is effectively a signal with virtually no amplitude, but satisfies the criteria that there be a stimulation signal before active recharge can begin. Thus, the ghost pulse may cause the state machine implemented in the processing circuitry to automatically transition the control electrode circuitry to an active recharge state and/or a passive recharge state. In some examples, because the ghost pulse has no amplitude, $I_{SRCAR}$ of during an active recharge state following the ghost pulse may apply a "zero-milliamp" current through the circuit, in effect not applying a current at all, and thus effectively not performing an active recharge.

The term "zero-milliamp" should not be interpreted to literally mean zero milliamp. Rather "zero-milliamp" refers to a stimulation signal having very low amplitude, and in some examples, low enough amplitude that there is no impact on patient physiology. In some examples, zero-milliamp signal may be zero milliamps, but the techniques are not so limited. A ghost pulse is another term for the zero-milliamp signal.

FIG. 6 is a conceptual diagram illustrating an example passive recharge state of operation of the stimulation circuit of FIG. 4, in accordance with one or more techniques of this disclosure. In the example of FIG. 6, the passive recharge state may result in a residual voltage difference across coupling capacitors 434 (e.g., charge left on coupling capacitors 434) draining. Furthermore, a voltage difference across $c_{par}$ may drain, resulting in $V_{body}$ approaching the value of IMD ground. Slight differences in the charge applied through the circuit in one direction during stimulus and the charge applied in the other direction during active recharge over many cycles may result in build-up of charge on coupling capacitors 434, even if stimulus and active recharge charges are intended to be balanced. The passive recharge state may release the built-up charge.

Subsequent to entering the active recharge state, the state machine implemented in the processing circuitry may automatically transition stimulation electrode circuitry 430 into a passive recharge state. Active recharge states may require a relatively large power expenditure from the power source of the IMD to generate the opposing current. In order to conserve power for extending the life of the IMD, the passive recharge state may replace the active recharge state in stimulation electrode circuitry 430. For example, the active recharge state may last for a shorter duration than necessary to completely remove the charge stored on coupling capacitors 434 due to a stimulus. In some examples, the current applied during active recharge may not be exactly equal to the current applied during stimulus.

To enter a passive recharge state, processing circuitry may be configured to form one or more loops within the circuit that includes stimulation electrode circuitry 430, wherein the loops allow residual charge in the circuit to drain. In some examples, to form the one or more loops, the processing circuitry of the IMD may close switches 604, connecting coupling capacitors 434 to one another in an inner current loop 684. Any differential charge stored on coupling capacitors 434 may flow through inner loop 684 and dissipate. Closing switches 604 may also form an outer loop 685 between $V_{body}$ and IMD ground, which may rapidly drain charge stored on $C_{par}$ (e.g., 5-10 μs) to make $V_{body}$ approach the value of IMD ground. This may help to improve the accuracy of the sensing circuitry when sensing for an ECAP by establishing the value of $V_{body}$ in relation to IMD ground.

In the example of FIG. 6, closing switches 604 connects the circuitry to the right of the 2040 resistors and switches 604 to IMD ground. In some examples, the circuit may include a constant voltage source between IMD ground and the 2040 resistors and switches 604. The constant voltage source may prevent the interior side of coupling capacitors 434 from being below IMD ground in certain modes of operation, unintentionally turning on electrostatic discharge (ESD) protection diodes and diodes to the silicon substrate that may be part of the IMD circuitry.

In some examples, stimulation electrodes 442 are control electrodes configured to deliver control pulses to the patient and stimulation electrode circuitry 430 is control electrode circuitry. Processing circuitry may instruct stimulation circuitry 444 to deliver an electrical stimulation signal having an amplitude substantially equal to zero (e.g., a ghost pulse) to the patient on the control electrodes. Instructing stimulation circuitry 444 to deliver the ghost pulse may cause a state machine implemented in the processing circuitry to automatically transition the control electrode circuitry to a passive recharge state. In some examples, the state machine may automatically transition the control electrode circuitry first to an active recharge state, then to a passive recharge state following the ghost pulse. While control electrode circuitry is in a passive recharge state following the ghost pulse, the processing circuitry may auto-zero sensing circuitry 400.

Figure 7:
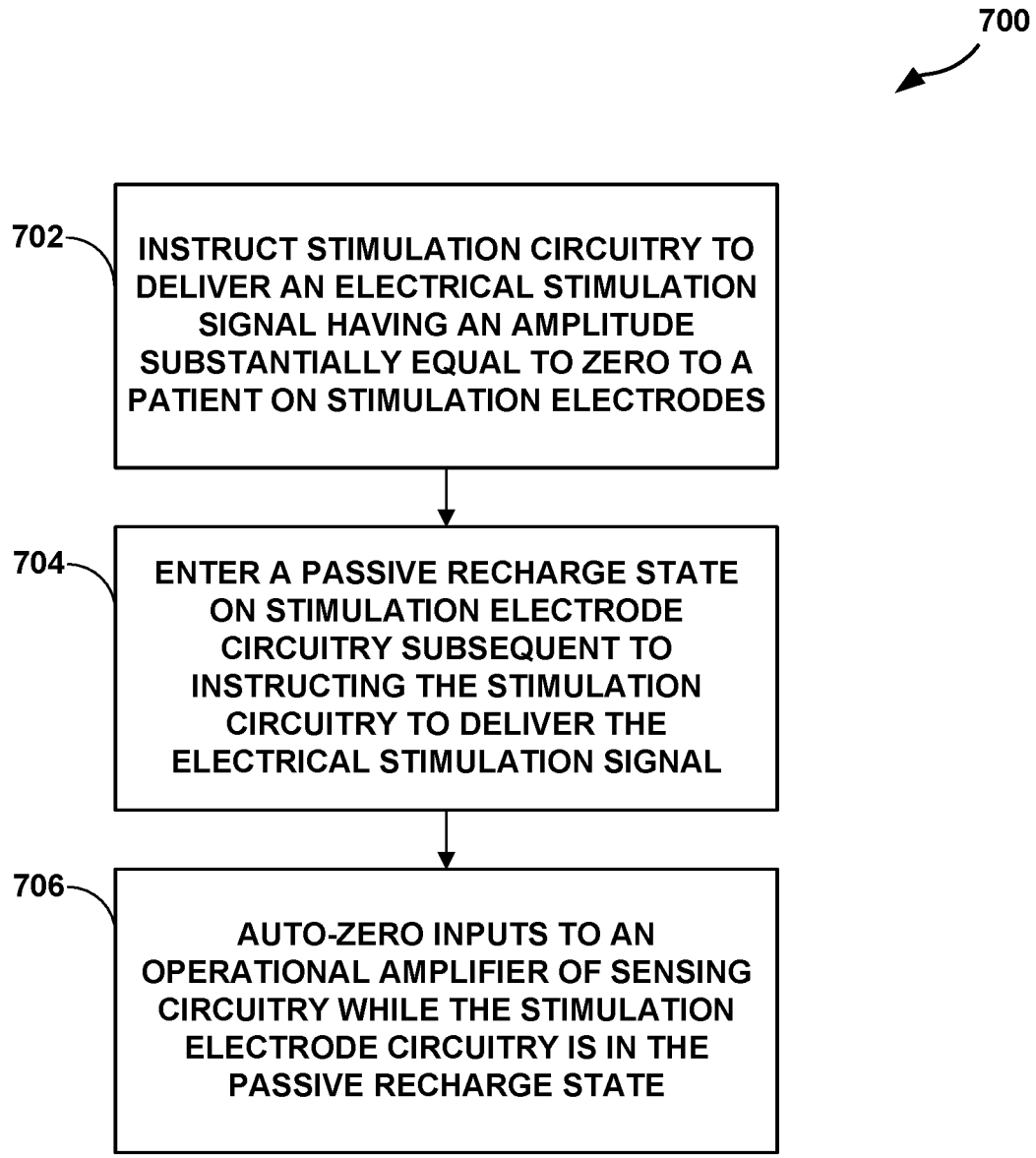
FIG. 7 is a flowchart illustrating an example operation for calibrating sensing circuitry of the IMD, in accordance with one or more techniques of this disclosure.

FIG. 7 is a flowchart illustrating an example operation for calibrating sensing circuitry of an IMD, in accordance with one or more techniques of this disclosure. The IMD may include processing circuitry and stimulation circuitry coupled to stimulation electrodes, where a method 700 includes instructing, with processing circuitry, stimulation circuitry of a medical device to deliver, on stimulation electrodes of the medical device, an electrical stimulation signal having an amplitude substantially equal to zero to a patient (702).

The IMD may include a plurality of electrodes configured to provide electrical stimulation therapy to a patient and/or sense for an ECAP signal from patient tissue. Each of the plurality of electrodes may be couplable to sensing circuitry to act as a set of sensing electrodes. Each of the plurality of electrodes may also be couplable to stimulation circuitry to act as stimulation electrodes. The stimulation electrodes may include one or more of a set of governing electrodes configured to deliver a governed therapy to the patient, and a set of control electrodes configured to deliver a control pulse to the patient. Electrical stimulation therapy may include the governed therapy and the control pulse. The control pulse may elicit an ECAP signal from patient tissue that is used to inform the parameters of the governed therapy. The sensing electrodes, the set of governing electrodes, and the set of control electrodes may each include a set of two or more electrodes of the plurality of electrodes of the IMD. The method 700 may include selecting, with the processing circuitry of the IMD, a first set of electrodes to act as the governing electrodes, a second set to act as the control electrodes, and a third set of electrodes to act as the sensing electrodes. In some examples, the first set of electrodes may include the same electrodes as the second set of electrodes. That is, the stimulation electrodes acting as the governing electrodes may also act as the control electrodes.

Electrical stimulation therapy may be informed by the measured ECAPs, that is, parameters of the electrical stimulation therapy (e.g., governed therapy) may be adjusted in response to measured ECAPs. In order to accurately measure ECAPs and provide more effective therapy, sensing circuitry configured to sense ECAPs may be effectively calibrated. To be effectively calibrated, sensing circuitry of an IMD should be calibrated when the IMD circuitry is in the same state as when the sensing circuitry would be sensing an ECAP signal. Generally, an IMD may sense for ECAP signals when control electrode circuitry of the IMD is in a state of passive recharge, i.e., after control electrodes of the IMD deliver a control pulse configured to elicit the ECAP signal. However, there may not be enough time between a control pulse and the subsequent ECAP signal for the processing circuitry of the IMD to calibrate the sensing circuitry. Therefore, the processing circuitry should calibrate the sensing circuitry at another time when control electrode circuitry is in a passive recharge state.

Method 700 may further include entering, with the processing circuitry subsequent to instructing the stimulation circuitry to deliver the electrical stimulation signal, a passive recharge state on the stimulation electrode circuitry (704).

To elicit a passive recharge state in the control electrode circuitry, the IMD may be programmed to deliver an electrical stimulation signal having an amplitude substantially equal to zero on the control electrodes. For example, processing circuitry of the IMD may instruct the control electrode circuitry to deliver an electrical stimulation signal having an amplitude substantially equal to zero (also called a "ghost pulse"). Delivering a ghost pulse on the control electrodes may initiate an active recharge and passive recharge cycle on the control electrode circuitry without adding any unnecessary charge to patient tissue or the circuitry of the IMD. Once the control electrode circuitry enters the passive recharge state following the ghost pulse, processing circuitry may calibrate the sensing circuitry. That is, an internal state machine of the IMD circuitry may be configured to automatically transition the control electrode circuitry into a passive recharge state after stimulation is delivered. However, for purposes of calibration, no stimulation signal is needed, but the state machine may need to first have a stimulation pulse that is delivered before the state machine can transition the stimulation electrode circuitry to the passive recharge state. Accordingly, by instructing the stimulation circuitry to deliver the electrical stimulation signal having an amplitude substantially equal to zero (also called a "ghost pulse"), the processing circuitry may satisfy the conditions for the state machine of the circuitry to determine that a stimulation signal was delivered, even though no actual stimulation signal was delivered. The state machine may then transition the control electrode circuitry to the passive recharge state so that the sensing circuitry can be calibrated in the correct state.

As the circuitry of the IMD provides therapy to patient tissue, DC current may flow to the body. This can cause damage to leads of the IMD and to patient tissue. Coupling capacitors may prevent DC current from flowing to the body by holding accumulated charge. In order to relieve the accumulated charge on the coupling capacitors, the stimulation electrode circuitry may enter the active and/or passive recharge states. Entering an active recharge state may include applying, with stimulation circuitry, a voltage across the coupling capacitors of the stimulation electrodes, wherein the voltage applied is opposite in charge to a charge stored on the coupling capacitors of the stimulation electrodes. For example, the stimulation circuitry may include a current source and a current sink, wherein, during stimulation, the current source is configured to send a first current having a first charge through the coupling capacitors and electrodes of the IMD to provide therapy to a patient. During active recharge, method 700 may include switching the current source and current sink, and sending a second current via the new current source having the first charge through the coupling capacitors in the opposite direction to actively dissipate accumulated charge on the coupling capacitors. In some examples, following a ghost pulse, the second current may be substantially equal to zero, in effect not performing an active recharge, but satisfying a condition in the state machine for the circuitry to transition to a passive recharge state.

Active recharge states require a relatively large power expenditure from a power source of the IMD to generate the opposing current. In order to conserve power for extending the life of the IMD, the passive recharge state may replace the active recharge state in stimulation electrode circuitry. For example, the active recharge state may last for a shorter duration than necessary to completely remove the charge stored on the coupling capacitors due to a stimulus. To enter a passive recharge state, the method may include connecting, by the processing circuitry, coupling capacitors of the stimulation electrode circuitry to one another in a circuit loop. In some examples, to enter a passive recharge state, method 700 may include closing one or more switches in the IMD circuitry, connecting the coupling capacitors to IMD ground and resulting in a loop between the coupling capacitors. In some examples, method 700 may include closing one or more switches in the IMD circuitry, connecting the coupling capacitors to a constant voltage source and resulting in a loop between the coupling capacitors. Any charge stored on the coupling capacitors may flow through the loop and dissipate.

In some examples, to enter a passive recharge state, method 700 may include forming one or more loops within the circuit that includes the stimulation electrode circuitry, wherein the loops allow residual charge in the circuit to drain. In some examples, method 700 includes closing one or more switches in the IMD circuitry, forming a loop between a common body voltage and IMD ground, which may rapidly drain charge stored on a parasitic capacitance to make the common body voltage approach the value of IMD ground. In some examples, method 700 includes closing one or more switches in the IMD circuitry, forming a loop between a common body voltage and a constant voltage source (e.g., having a constant voltage $V_S$), which may rapidly drain charge stored on a parasitic capacitance to make the common body voltage approach the value of IMD ground. When a constant voltage source is used, capacitors 434 may have an additional voltage $V_S$ throughout the stimulus and recharge cycles. This increase in voltage interior to capacitors 434 may prevent ESD diodes and diodes to the substrate from unintentionally turning on.

While the stimulation electrode circuitry is in the passive recharge state, the method may include auto-zeroing, with the processing circuitry, inputs to an operational amplifier of the sensing circuitry electrically coupled to sensing electrodes of the IMD (706). The inputs may include an "A terminal" and a "B terminal." Auto-zeroing the inputs to the operational amplifier may calibrate the sensing circuitry for sensing ECAP signals from patient tissue. As the IMD operates, charge may build up in the wires of the sensing circuitry in one or more calibration capacitors of the sensing circuitry. To auto-zero the inputs to the operational amplifier, processing circuitry may close switches next to the inputs that are connected to IMD ground to connect the inputs of the operational amplifier to IMD ground. Any offsets in the wires of the sensing circuitry near the inputs may be stored on the calibration capacitors. For example, the method may include connecting, with processing circuitry, a first input (e.g., terminal A) of the operational amplifier to IMD ground by closing a first switch. By connecting the first input to IMD ground, processing circuitry may cause voltage offsets in a first wire of the sensing circuitry to be stored in a first calibration capacitor on the first wire. In another example, the method may include connecting, with processing circuitry, a second input (e.g., terminal A) of the operational amplifier to IMD ground by closing a second switch. By connecting the second input to IMD ground, processing circuitry may cause voltage offsets in a second wire of the sensing circuitry to be stored in a second calibration capacitor on the second wire.

To auto-zero the inputs of the operational amplifier, the method may include zeroing, with processing circuitry, a differential signal between the operational amplifier inputs and zeroing a common-mode signal on both the operational amplifier inputs. A differential signal between the inputs may be calculated by determining a difference in voltage between the A terminal and B terminal of the inputs (i.e., a difference in voltage between the first and second inputs). For example, if the input to terminal A is 100.25 millivolts and the input to terminal B is 99.75 millivolts, the differential signal would be 0.5 millivolts. By storing offsets on the calibration capacitors as described above, processing circuitry may ensure that a differential signal across terminals A and B of the inputs is low enough for the operational amplifier to receive and amplify an accurate ECAP signal, because differences in the inputs to the A and B terminals would be stored on the calibration capacitors. In some examples, the differential signal after auto-zeroing may be less than thirty microvolts.

A common mode signal on the inputs may be calculated by determining an average voltage across the A terminal and B terminal of the inputs (i.e., an average voltage across the first and second inputs). For example, if the input to terminal A is 100.25 millivolts and the input to terminal B is 99.75 millivolts, the common mode signal would be 100 millivolts. By connecting the sensing circuitry to IMD ground (i.e., auto-zeroing the inputs to the operational amplifier) processing circuitry may ensure that the common mode offset to the inputs of the operational amplifier is near zero, removing the common mode offset received from the patient tissue through the electrodes. The operational amplifier may be designed to accept common mode input ranges based on known common mode input ranges of body tissue after the auto-zero operation. In some examples, the input range of operational amplifier may be around plus or minus 100 millivolts.

Method 700 may include performing therapy on patient tissue using the IMD according to a cycle. For example, method 700 may include delivering, with stimulation circuitry, a governed therapy on the governing electrodes to patient tissue after sensing for the evoked compound action potential. After delivering the governed therapy, the method may include entering, with processing circuitry, a passive recharge state on the governing electrode circuitry. In some examples, the method may include entering an active recharge state on the governing electrode circuitry after delivering the governed therapy and before entering the passive recharge state or delivering another governed therapy. While the governing electrode circuitry is in a passive recharge state, and in order to elicit an active recharge state on the control electrode circuitry, the method may include instructing, with processing circuitry, stimulation circuitry to deliver, on the control electrodes, an electrical stimulation signal having an amplitude substantially equal to zero to the patient (e.g., a ghost pulse). Instructing stimulation circuitry to deliver an electrical stimulation signal (e.g., governed therapy, control pulse, ghost pulse) on stimulation electrodes (e.g., governing electrodes, control electrodes), may cause the state machine of the IMD circuitry to automatically transition the stimulation electrode circuitry (e.g., governing electrode circuitry, control electrode circuitry) into an active and/or passive recharge state. For example, the ghost pulse may induce the state machine of the IMD circuitry to automatically transition the control electrode circuitry into an intended recharge state for calibration. For example, following the ghost pulse, the method may include entering, with processing circuitry, a first active recharge state on the control electrode circuitry, followed by a first passive recharge state on the control electrode circuitry. Because the ghost pulse is an electrical stimulation signal having an amplitude substantially equal to zero, the current source of the circuit during the active recharge state may apply a "zero-milliamp" current through the circuit, in effect not applying a current at all, and thus effectively not performing an active recharge. In some examples, following the ghost pulse, the method may include entering, with processing circuitry, the first passive recharge state on the control electrode circuitry. While the control electrode circuitry is in the first passive recharge state, the method may include calibrating the sensing circuitry. Thus, the method may include auto-zeroing inputs to the operational amplifier after the stimulation circuitry delivers a governed therapy on the governing electrodes and before the stimulation circuitry delivers a control pulse on the control electrodes, for example, during the first passive recharge state on the control electrodes. After the first passive recharge state on the control electrodes, the method may include delivering, with stimulation circuitry, electrical stimulation therapy to a patient on the control electrodes, the electrical stimulation therapy comprising the control pulse. Following the control pulse, the method may include entering, with processing circuitry, a second active recharge state on the control electrode circuitry, followed by entering a second passive recharge state on the control electrode circuitry. During the second passive recharge state, the method may include sensing, with processing circuitry, for an ECAP using sensing electrodes coupled to sensing circuitry of the IMD. Following sensing for an ECAP, the method may include delivering, with stimulation circuitry, a governed therapy to the patient tissue on the governing electrodes. The governed therapy may be informed by the ECAP signal. The cycle may then repeat. Although in the previous example the cycle started with delivery of a governed therapy, in some examples the cycle may begin at any step.

Instructions may be stored in a memory of the IMD directing processing circuitry to enter the one or more recharge states on the circuitry of one or more electrodes following an electrical stimulation therapy pulse delivered on the one or more electrodes.

Figure 8:
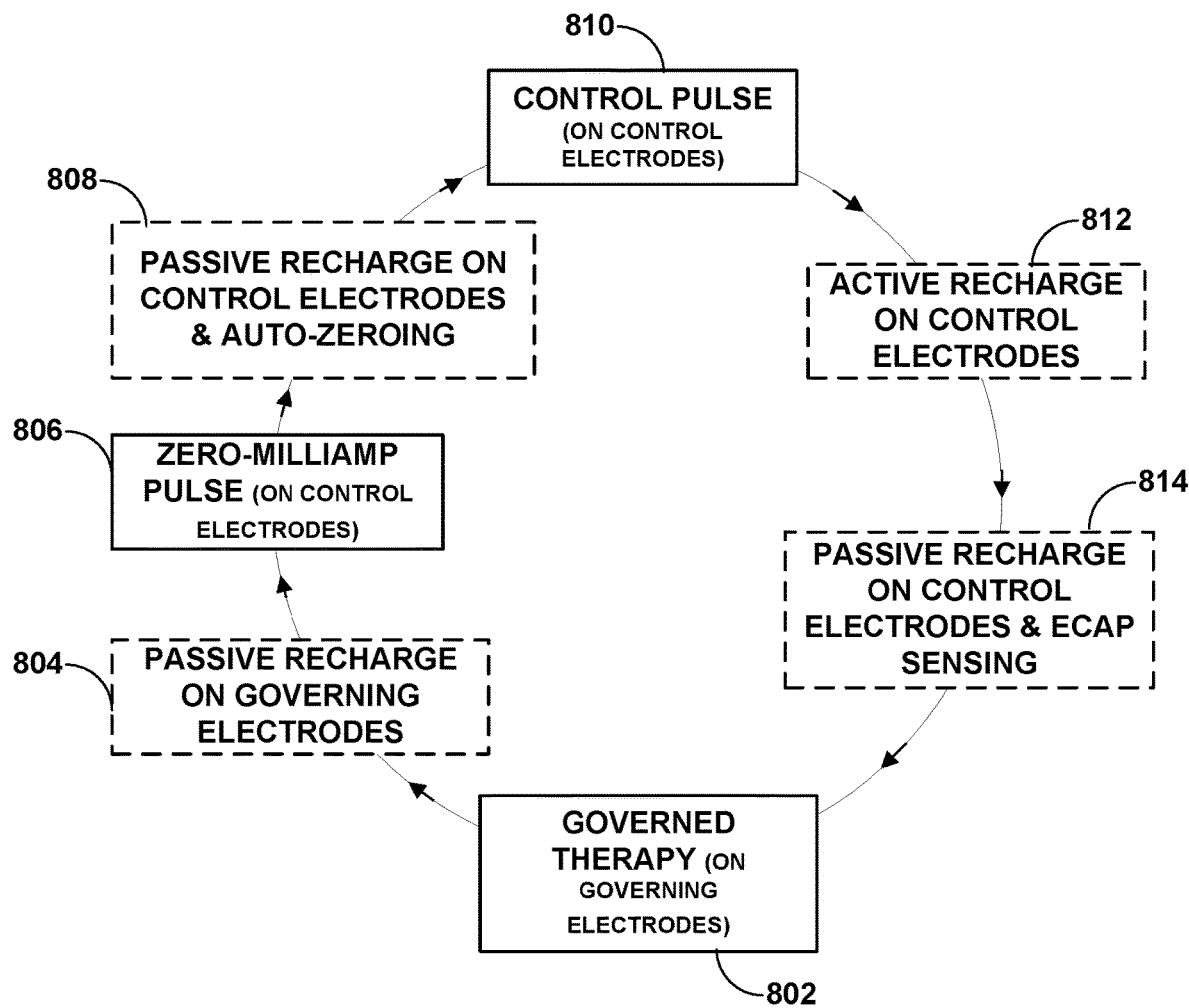
FIG. 8 is a flowchart illustrating an example operation for calibrating sensing circuitry of the IMD and delivering therapy, in accordance with one or more techniques of this disclosure.

FIG. 8 is a flowchart illustrating an example operation for calibrating sensing circuitry of the IMD and delivering therapy, in accordance with one or more techniques of this disclosure.

The IMD may be configured to perform therapy on patient tissue according to a cycle. For example, processing circuitry of the IMD may cause the stimulation circuitry to deliver, on the governing electrodes, a governed therapy to the patient after sensing for the evoked compound action potential (802). After delivery of the governed therapy, the governing electrode circuitry may enter (804). While the governing electrode circuitry is in a passive recharge state, and in order to elicit a passive recharge state on the control electrodes, processing circuitry is further configured to cause stimulation circuitry of the medical device to deliver, on the control electrodes, an electrical stimulation signal having an amplitude substantially equal to zero (e.g., a ghost pulse) to a patient (806). The ghost pulse may induce the state machine of the IMD circuitry to enter an intended recharge state for calibration. Following the ghost pulse, processing circuitry may automatically transition the control electrode circuitry into a first active recharge state, and, subsequent to the active recharge state, transition the control electrode circuitry into a first passive recharge state (808). Because the ghost pulse has an amplitude substantially equal to zero, the current source of the circuit during the active recharge state may apply a "zero-milliamp" current through the circuit, in effect not applying a current at all. In some examples, the processing circuitry may transition the control electrode circuitry directly to a passive recharge state following the ghost pulse. The processing circuitry may be configured to auto-zero inputs to an operational amplifier of sensing circuitry of the IMD during the first passive recharge state on the control electrodes. By auto-zeroing inputs to the operational amplifier, the processing circuitry may discharge the charge on a set of calibration capacitors, effectively zeroing a differential signal and common-mode signal on the operational amplifier inputs, and calibrating the sensing circuitry for sensing an ECAP signal.

After the first passive recharge state on the control electrodes, the processing circuitry may cause the stimulation circuitry to deliver, on the control electrodes, electrical stimulation therapy to a patient, the electrical stimulation therapy comprising the control pulse (810). The control pulse may be followed by a second active recharge state (i.e., following the control pulse, processing circuitry may be configured to automatically transition the control electrode circuitry into a second active recharge state) (812), and the second active recharge state may be followed by a second passive recharge state on the control electrode circuitry (814). The processing circuitry may be configured to cause the sensing circuitry to sense, during the second passive recharge state on the control electrode circuitry, for an ECAP. Following sensing for an ECAP, the processing circuitry may cause the stimulation circuitry to deliver a governed therapy to the patient tissue on the governing electrodes. The cycle may then repeat. Although in the previous example the cycle started with delivery of a governed therapy, in some examples the cycle may begin at any step.

The following examples are described herein.

Example 1: A method includes: instructing, with processing circuitry, stimulation circuitry of a medical device to deliver, on stimulation electrodes of the medical device, an electrical stimulation signal having an amplitude substantially equal to zero to a patient; entering, with the processing circuitry subsequent to instructing the stimulation circuitry to deliver the electrical stimulation signal, a passive recharge state on stimulation electrode circuitry; and auto-zeroing, with the processing circuitry, inputs to an operational amplifier of sensing circuitry electrically coupled to sensing electrodes of the medical device while the stimulation electrode circuitry is in the passive recharge state.

Example 2: The method of example 1, wherein instructing the stimulation circuitry to deliver the electrical stimulation signal causes a state machine implemented in the processing circuitry to automatically transition the stimulation electrode circuitry to the passive recharge state.

Example 3: The method of any of examples 1 or 2, wherein entering the passive recharge state on the stimulation electrode circuitry includes connecting AC coupling capacitors of the stimulation electrode circuitry to one another in a circuit loop.

Example 4: The method of any of examples 1-3, wherein auto-zeroing the inputs to the operational amplifier includes:

connecting a first input to the operational amplifier to ground of the medical device, wherein connecting the first input to ground causes voltage offsets in a first wire to be stored in a first calibration capacitor on the first wire; and connecting a second input to the operational amplifier to ground, wherein connecting the second input to ground causes voltage offsets in a second wire to be stored in a second calibration capacitor on the second wire.

Example 5: The method of any of examples 1-4, wherein the stimulation electrodes include one or more of a set of governing electrodes configured to deliver a governed therapy to the patient and a set of control electrodes configured to deliver a control pulse to the patient, and auto-zeroing includes auto-zeroing after the governing electrodes deliver the governed therapy and before the control electrodes deliver the control pulse.

Example 6: The method of example 5, further including: delivering, with the stimulation circuitry on the control electrodes, the control pulse to the patient; entering, with the processing circuitry subsequent to delivering the electrical stimulation therapy, an active recharge state on the control electrode circuitry; entering, with the processing circuitry subsequent to the active recharge state, the passive recharge state on the control electrode circuitry; sensing, with the sensing electrodes during the passive recharge state on the control electrode circuitry, for an evoked compound action potential; and delivering, with the stimulation circuitry on the governing electrodes, a governed therapy to the patient after sensing for the evoked compound action potential, wherein the governed therapy is informed by the sensed evoked compound action potential.

Example 7: The method of example 6, wherein delivering the control pulse on the control electrodes causes a state machine implemented in the processing circuitry of the medical device to: automatically transition the control electrode circuitry to the active recharge state subsequent to delivering the control pulse; and automatically transition the control electrode circuitry to the passive recharge state subsequent to the active recharge state.

Example 8: The method of any of examples 6 or 7, wherein entering the active recharge state includes applying, with stimulation circuitry, a voltage across AC coupling capacitors of the control electrodes, wherein the voltage applied is opposite in charge to a charge stored on the AC coupling capacitors of the control electrodes.

Example 9: The method of any of examples 1-8, wherein: the stimulation electrodes include one or more of a set of governing electrodes configured to deliver a governed therapy to the patient and a set of control electrodes configured to deliver a control pulse to the patient, the set of governing electrodes, the set of control electrodes, and the sensing electrodes each include a set of two or more electrodes of a plurality of electrodes within the medical device, each of the plurality of electrodes is configured to act as a governing electrode of the set of governing electrodes, a control electrode of the set of control electrodes, or a sensing electrode of the sensing electrodes, and the method further includes selecting, with the processing circuitry: a first set of electrodes to act as the governing electrodes, a second set of electrodes to act as the control electrodes, and a third set of electrodes to act as the sensing electrodes.

Example 10: The method of example 9, wherein the first set of electrodes includes the same electrodes as the second set of electrodes.

Example 11: A system including a medical device, wherein the medical device includes: sensing circuitry including an operational amplifier and electrically couplable to sensing electrodes; stimulation circuitry electrically couplable to stimulation electrodes; and processing circuitry configured to: instruct the stimulation circuitry to deliver, on the stimulation electrodes, an electrical stimulation signal having an amplitude substantially equal to zero to a patient; enter, subsequent to instructing the stimulation circuitry to deliver the electrical stimulation signal, a passive recharge state on stimulation electrode circuitry; and auto-zero inputs to the operational amplifier of the sensing circuitry while the stimulation electrode circuitry is in the passive recharge state.

Example 12: The system of example 11, wherein instructing the stimulation circuitry to deliver the electrical stimulation signal causes a state machine implemented in the processing circuitry to automatically transition the stimulation electrode circuitry to the passive recharge state.

Example 13: The system of any of examples 11 or 12, wherein, to enter the passive recharge state on the stimulation electrode circuitry, the processing circuitry is further configured to connect AC coupling capacitors of the stimulation electrode circuitry to one another in a circuit loop.

Example 14: The system of any of examples 11-13, wherein, to auto-zero the inputs to the operational amplifier, the processing circuitry is further configured to: connect a first input to the operational amplifier to ground of the medical device, wherein connecting the first input to ground causes voltage offsets in a first wire of the sensing circuitry to be stored in a first calibration capacitor on the first wire; and connect a second input to the operation amplifier to ground, wherein connecting the second input to ground causes voltage offsets in a second wire of the sensing circuitry to be stored in a second calibration capacitor on the second wire.

Example 15: The system of any of examples 11-14, wherein the stimulation electrodes includes one or more of a set of governing electrodes configured to deliver a governed therapy to the patient and a set of control electrodes configured to deliver a control pulse to the patient, and to auto-zero the inputs, the processing circuitry is further configured to auto-zero after the governing electrodes deliver the governed therapy and before the control electrodes deliver the control pulse.

Example 16: The system of example 15, wherein the processing circuitry is further configured to: cause the stimulation circuitry to deliver, on the control electrodes, the control pulse to the patient; enter, subsequent to delivering the control pulse, an active recharge state on the control electrode circuitry, enter, subsequent to the active recharge state, the passive recharge state on the control electrode circuitry; cause the sensing circuitry to sense on the sensing electrodes, during the passive recharge state on the control electrode circuitry, for an evoked compound action potential; and cause the stimulation circuitry to deliver, on the governing electrodes, a governed therapy to the patient after sensing for the evoked compound action potential, wherein the governed therapy is informed by the sensed evoked compound action potential.

Example 17: The system of example 16, wherein delivering the control pulse on the control electrodes causes a state machine implemented in the processing circuitry of the medical device to: automatically transition the control electrode circuitry to the active recharge state subsequent to delivering the control pulse; and automatically transition the control electrode circuitry to the passive recharge state subsequent to the active recharge state.

Example 18: The system of any of examples 16 or 17, wherein to enter the active recharge state on the control electrodes, processing circuitry is further configured to: cause stimulation circuitry to apply a voltage across AC coupling capacitors of the control electrodes, wherein the voltage applied is opposite in charge to a charge stored on the AC coupling capacitors of the control electrodes.

Example 19: The system of any of examples 11-18, further including a plurality of electrodes, wherein: the stimulation electrodes include one or more of a set of governing electrodes configured to deliver a governed therapy to the patient and a set of control electrodes configured to deliver a control pulse to the patient, the set of governing electrodes, the set of control electrodes, and the sensing electrodes each include a set of two or more electrodes of the plurality of electrodes, each of the plurality of electrodes is configured to act as a governing electrode of the set of governing electrodes, a control electrode of the set of control electrodes, or a sensing electrode of the sensing electrodes, and the processing circuitry is further configured to select: a first set of electrodes to act as the set of governing electrodes, a second set of electrodes to act as the set of control electrodes, and a third set of electrodes to act as the sensing electrodes.

Example 20: A computer-readable storage medium including instructions that, when executed by processing circuitry, cause the processing circuitry to: instruct stimulation circuitry to deliver, on stimulation electrodes, an electrical stimulation signal having an amplitude substantially equal to zero to a patient; enter, subsequent to instructing the stimulation circuitry to deliver the electrical stimulation signal, a passive recharge state on stimulation electrode circuitry; and auto-zero inputs to an operational amplifier of sensing circuitry of the medical device while the stimulation electrode is in the passive recharge state.

The techniques described in this disclosure may be implemented, at least in part, in hardware, software, firmware or any combination thereof. For example, various aspects of the described techniques may be implemented within one or more processors or processing circuitry, including one or more microprocessors, digital signal processors (DSPs), application specific integrated circuits (ASICs), field programmable gate arrays (FPGAs), or any other equivalent integrated or discrete logic circuitry, as well as any combinations of such components. The term "processor" or "processing circuitry" may generally refer to any of the foregoing logic circuitry, alone or in combination with other logic circuitry, or any other equivalent circuitry. A control unit including hardware may also perform one or more of the techniques of this disclosure.

Such hardware, software, and firmware may be implemented within the same device or within separate devices to support the various operations and functions described in this disclosure. In addition, any of the described units, circuits or components may be implemented together or separately as discrete but interoperable logic devices. Depiction of different features as circuits or units is intended to highlight different functional aspects and does not necessarily imply that such circuits or units must be realized by separate hardware or software components. Rather, functionality associated with one or more circuits or units may be performed by separate hardware or software components or integrated within common or separate hardware or software components.

The techniques described in this disclosure may also be embodied or encoded in a computer-readable medium, such as a computer-readable storage medium, containing instructions that may be described as non-transitory media. Instructions embedded or encoded in a computer-readable storage medium may cause a programmable processor, or other processor, to perform the method, e.g., when the instructions are executed. Computer readable storage media may include random access memory (RAM), read only memory (ROM), programmable read only memory (PROM), erasable programmable read only memory (EPROM), electronically erasable programmable read only memory (EEPROM), flash memory, a hard disk, a CD-ROM, a floppy disk, a cassette, magnetic media, optical media, or other computer readable media.

What is claimed is:

1. A method comprising:
   instructing, with processing circuitry, stimulation circuitry of a medical device to deliver, on stimulation electrodes of the medical device, an electrical stimulation signal having an amplitude substantially equal to zero to a patient;
   entering, with the processing circuitry subsequent to instructing the stimulation circuitry to deliver the electrical stimulation signal, a passive recharge state on stimulation electrode circuitry; and
   auto-zeroing, with the processing circuitry, inputs to an operational amplifier of sensing circuitry electrically coupled to sensing electrodes of the medical device while the stimulation electrode circuitry is in the passive recharge state.

2. The method of claim 1, wherein instructing the stimulation circuitry to deliver the electrical stimulation signal causes a state machine implemented in the processing circuitry to automatically transition the stimulation electrode circuitry to the passive recharge state.

3. The method of claim 1, wherein entering the passive recharge state on the stimulation electrode circuitry comprises connecting AC coupling capacitors of the stimulation electrode circuitry to one another in a circuit loop.

4. The method of claim 1, wherein auto-zeroing the inputs to the operational amplifier comprises:
   connecting a first input to the operational amplifier to ground of the medical device, wherein connecting the first input to ground causes voltage offsets in a first wire to be stored in a first calibration capacitor on the first wire; and
   connecting a second input to the operational amplifier to ground, wherein connecting the second input to ground causes voltage offsets in a second wire to be stored in a second calibration capacitor on the second wire.

5. The method of claim 1, wherein:
   the stimulation electrodes comprise one or more of a set of governing electrodes configured to deliver a governed therapy to the patient and a set of control electrodes configured to deliver a control pulse to the patient,
   auto-zeroing comprises auto-zeroing after the governing electrodes deliver the governed therapy and before the control electrodes deliver the control pulse.

6. The method of claim 5, further comprising:
   delivering, with the stimulation circuitry on the control electrodes, the control pulse to the patient;
   entering, with the processing circuitry subsequent to delivering the electrical stimulation therapy, an active recharge state on the control electrode circuitry;
   entering, with the processing circuitry subsequent to the active recharge state, the passive recharge state on the control electrode circuitry;
   sensing, with the sensing electrodes during the passive recharge state on the control electrode circuitry, for an evoked compound action potential; and delivering, with the stimulation circuitry on the governing electrodes, a governed therapy to the patient after sensing for the evoked compound action potential, wherein the governed therapy is informed by the sensed evoked compound action potential.

7. The method of claim 6, wherein delivering the control pulse on the control electrodes causes a state machine implemented in the processing circuitry of the medical device to:
automatically transition the control electrode circuitry to the active recharge state subsequent to delivering the control pulse; and
automatically transition the control electrode circuitry to the passive recharge state subsequent to the active recharge state.

8. The method of claim 6, wherein entering the active recharge state comprises applying, with stimulation circuitry, a voltage across AC coupling capacitors of the control electrodes, wherein the voltage applied is opposite in charge to a charge stored on the AC coupling capacitors of the control electrodes.

9. The method of claim 1, wherein:
the stimulation electrodes comprise one or more of a set of governing electrodes configured to deliver a governed therapy to the patient and a set of control electrodes configured to deliver a control pulse to the patient,
the set of governing electrodes, the set of control electrodes, and the sensing electrodes each comprise a set of two or more electrodes of a plurality of electrodes within the medical device,
each of the plurality of electrodes is configured to act as a governing electrode of the set of governing electrodes, a control electrode of the set of control electrodes, or a sensing electrode of the sensing electrodes, and
the method further comprises selecting, with the processing circuitry:
a first set of electrodes to act as the governing electrodes,
a second set of electrodes to act as the control electrodes, and
a third set of electrodes to act as the sensing electrodes.

10. The method of claim 9, wherein the first set of electrodes comprises the same electrodes as the second set of electrodes.

11. A system comprising a medical device, wherein the medical device comprises:
sensing circuitry comprising an operational amplifier, the sensing circuitry being electrically couplable to sensing electrodes;
stimulation circuitry electrically couplable to stimulation electrodes; and
processing circuitry configured to:
instruct the stimulation circuitry to deliver, on the stimulation electrodes, an electrical stimulation signal having an amplitude substantially equal to zero to a patient;
enter, subsequent to instructing the stimulation circuitry to deliver the electrical stimulation signal, a passive recharge state on stimulation electrode circuitry; and
auto-zero inputs to the operational amplifier of the sensing circuitry while the stimulation electrode circuitry is in the passive recharge state.

12. The system of claim 11, wherein instructing the stimulation circuitry to deliver the electrical stimulation signal causes a state machine implemented in the processing circuitry to automatically transition the stimulation electrode circuitry to the passive recharge state.

13. The system of claim 11, wherein, to enter the passive recharge state on the stimulation electrode circuitry, the processing circuitry is further configured to connect AC coupling capacitors of the stimulation electrode circuitry to one another in a circuit loop.

14. The system of claim 11, wherein, to auto-zero the inputs to the operational amplifier, the processing circuitry is further configured to:
connect a first input to the operational amplifier to ground of the medical device, wherein connecting the first input to ground causes voltage offsets in a first wire of the sensing circuitry to be stored in a first calibration capacitor on the first wire; and
connect a second input to the operation amplifier to ground, wherein connecting the second input to ground causes voltage offsets in a second wire of the sensing circuitry to be stored in a second calibration capacitor on the second wire.

15. The system of claim 11, wherein,
the stimulation electrodes comprise one or more of a set of governing electrodes configured to deliver a governed therapy to the patient and a set of control electrodes configured to deliver a control pulse to the patient, and
to auto-zero the inputs, the processing circuitry is further configured to auto-zero after the governing electrodes deliver the governed therapy and before the control electrodes deliver the control pulse.

16. The system of claim 15, wherein the processing circuitry is further configured to:
cause the stimulation circuitry to deliver, on the control electrodes, the control pulse to the patient;
enter, subsequent to delivering the control pulse, an active recharge state on the control electrode circuitry,
enter, subsequent to the active recharge state, the passive recharge state on the control electrode circuitry;
cause the sensing circuitry to sense on the sensing electrodes, during the passive recharge state on the control electrode circuitry, for an evoked compound action potential; and
cause the stimulation circuitry to deliver, on the governing electrodes, a governed therapy to the patient after sensing for the evoked compound action potential, wherein the governed therapy is informed by the sensed evoked compound action potential.

17. The system of claim 16, wherein delivering the control pulse on the control electrodes causes a state machine implemented in the processing circuitry of the medical device to:
automatically transition the control electrode circuitry to the active recharge state subsequent to delivering the control pulse; and
automatically transition the control electrode circuitry to the passive recharge state subsequent to the active recharge state.

18. The system of claim 16, wherein to enter the active recharge state on the control electrodes, processing circuitry is further configured to:
cause stimulation circuitry to apply a voltage across AC coupling capacitors of the control electrodes, wherein the voltage applied is opposite in charge to a charge stored on the AC coupling capacitors of the control electrodes.

19. The system of claim 11, further comprising a plurality of electrodes, wherein:
the stimulation electrodes comprise one or more of a set of governing electrodes configured to deliver a governed therapy to the patient and a set of control electrodes configured to deliver a control pulse to the patient,
the set of governing electrodes, the set of control electrodes, and the sensing electrodes each comprise a set of two or more electrodes of the plurality of electrodes,
each of the plurality of electrodes is configured to act as a governing electrode of the set of governing electrodes, a control electrode of the set of control electrodes, or a sensing electrode of the sensing electrodes, and
the processing circuitry is further configured to select:
a first set of electrodes to act as the set of governing electrodes,
a second set of electrodes to act as the set of control electrodes, and
a third set of electrodes to act as the sensing electrodes.

20. A non-transitory computer-readable storage medium comprising instructions that, when executed by processing circuitry of a medical device, cause the processing circuitry to:
instruct stimulation circuitry to deliver, on stimulation electrodes, an electrical stimulation signal having an amplitude substantially equal to zero to a patient;
enter, subsequent to instructing the stimulation circuitry to deliver the electrical stimulation signal, a passive recharge state on stimulation electrode circuitry; and
auto-zero inputs to an operational amplifier of sensing circuitry of the medical device while the stimulation electrode is in the passive recharge state.

\* \* \* \* \*